(12) United States Patent
Sheppeck et al.

(10) Patent No.: US 10,927,136 B2
(45) Date of Patent: Feb. 23, 2021

(54) PHOSPHORUS PRODRUGS OF PYRAZOLO-SUBSTITUTED PYRIMIDINE SGC STIMULATORS

(71) Applicant: Cyclerion Therapeutics, Inc., Cambridge, MA (US)

(72) Inventors: James Edward Sheppeck, Newtown, PA (US); Paul Allan Renhowe, Sudbury, MA (US); Ara Mermerian, Waltham, MA (US); Timothy Claude Barden, Salem, MA (US); Glen Robert Rennie, Somerville, MA (US); Rajesh R. Iyengar, West Newton, MA (US); Takashi Nakai, Newton, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/315,210

(22) PCT Filed: Jul. 6, 2017

(86) PCT No.: PCT/US2017/040809
§ 371 (c)(1),
(2) Date: Jan. 4, 2019

(87) PCT Pub. No.: WO2018/009596
PCT Pub. Date: Jan. 11, 2018

(65) Prior Publication Data
US 2019/0300555 A1    Oct. 3, 2019

Related U.S. Application Data

(60) Provisional application No. 62/359,419, filed on Jul. 7, 2016.

(51) Int. Cl.
*A61K 31/506* (2006.01)
*C07D 239/42* (2006.01)
*C07F 9/6558* (2006.01)
*A61P 9/10* (2006.01)
*A61P 25/28* (2006.01)
*A61P 3/00* (2006.01)
*A61P 9/12* (2006.01)

(52) U.S. Cl.
CPC ............ *C07F 9/65583* (2013.01); *A61P 3/00* (2018.01); *A61P 9/10* (2018.01); *A61P 9/12* (2018.01); *A61P 25/28* (2018.01); *C07F 9/65586* (2013.01)

(58) Field of Classification Search
CPC ............................ A61K 31/506; C07D 239/42
USPC .......................................... 514/256; 544/333
See application file for complete search history.

(56) References Cited

FOREIGN PATENT DOCUMENTS

WO    2014/144100 A2    9/2014
WO    2015/106268 A1    7/2015
WO    WO 18/009596    *    1/2018

OTHER PUBLICATIONS

Jordan, V. C. Nature Reviews: Drug Discovery, 2, 2003, 205.*
Hackam, et al. JAMA, 296(14), 2006, 1731-1732.*
Huttunen et al., Prodrugs—from serendipity to rational design. Pharmacol Rev. Sep. 2011; 63(3):750-71.
International Search Report and Written Opinion for Application No. PCT/US2017/040809, dated Sep. 19, 2017, 10 pages.

* cited by examiner

*Primary Examiner* — Douglas M Willis
(74) *Attorney, Agent, or Firm* — McCarter & English, LLP; Steven G. Davis; Xin Zhang

(57) ABSTRACT

The present patent application discloses the compounds according to Formula (I) shown below, or pharmaceutically acceptable salts thereof wherein $J^B$, n, $R^1$, $R^2$, $R^3$, $R^4$, $R^5$, m and X as defined herein.

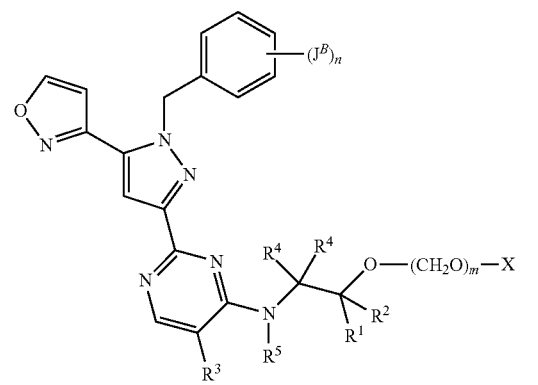

16 Claims, No Drawings

PHOSPHORUS PRODRUGS OF PYRAZOLO-SUBSTITUTED PYRIMIDINE SGC STIMULATORS

CROSS-REFERENCE TO RELATED APPLICATIONS

This application is a 35 U.S.C. § 371 national stage filing of International Application No. PCT/US2017/040809, filed on Jul. 6, 2017, which claims the benefit of the filing date, under 35 U.S.C. § 119(e), of U.S. Provisional Application No. 62/359,419, filed on Jul. 7, 2016. The entire content of each of the foregoing applications is hereby incorporated by reference.

FIELD OF THE INVENTION

The present disclosure relates to phosphorus containing prodrugs of stimulators of soluble guanylate cyclase (sGC), pharmaceutical formulations comprising them and their uses thereof, alone or in combination with one or more additional agents, for treating various diseases, wherein the diseases or disorders are ones that would benefit from sGC stimulation or from an increase in the concentration of nitric oxide (NO) and/or cyclic guanosine monophosphate (cGMP).

BACKGROUND OF THE INVENTION sGC is the primary receptor for NO in vivo. sGC can be activated via both NO-dependent and NO-independent mechanisms. In response to this activation, sGC converts guanosine-5'-triphosphate (GTP) into the secondary messenger cGMP. The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long-term potentiation; and constitutive endothelial NOS (eNOS or NOS III) which regulates smooth muscle relaxation and blood pressure. Experimental and clinical evidence indicates that reduced concentrations or bioavailability of NO and/or responsiveness to endogenously produced NO contributes to the development of disease.

NO-independent, heme-dependent, sGC stimulators, have displayed several important differentiating characteristics when compared with NO-independent, heme-independent sGC activators. These include crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. Compounds that stimulate sGC in an NO-independent manner offer considerable advantages over other current alternative therapies that target the aberrant NO pathway. There is a need to develop novel stimulators of sGC. In particular, there is a need to develop stimulators of sGC with improved solubility and pharmaceutical properties useful for clinical applications.

SUMMARY OF THE INVENTION

In one embodiment, the invention relates to compounds of Formula I:

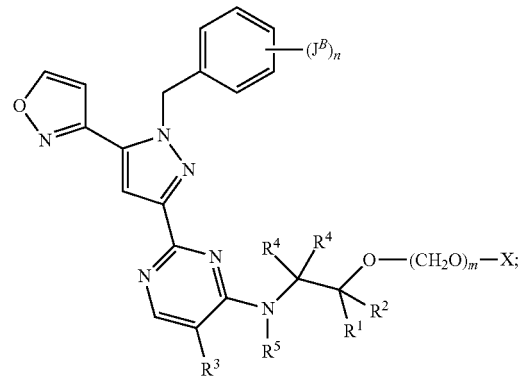

Formula I wherein,
X is selected from —P(O)(OH)$_2$, —P(O)(OH)O$^-$M$^+$, —P(O)(O$^-$)$_2$(M$^+$)$_2$ or —P(O)(O$^-$)$_2$D$^{2+}$; wherein M+ is a pharmaceutically acceptable monovalent cation and D$^{2+}$ is a pharmaceutically acceptable divalent cation;
each J$^B$ is independently selected from halogen;
m is selected from 0 or 1;
n is selected from 0, 1, 2, 3 or 4;
R$^1$ is selected from C$_{1-4}$ alkyl, C$_{1-4}$ fluoroalkyl, —C(O)NH$_2$ or hydrogen; and
R$^2$ is selected from C$_{1-4}$ alkyl, C$_{1-4}$ fluoroalkyl or hydrogen; or, alternatively,
R$^1$ and R$^2$, together with the carbon atom to which they are attached, form an unsubstituted C$_{3-7}$ cycloaliphatic ring or an unsubstituted 3 to 7-membered heterocyclic ring, containing up to 2 heteroatoms independently selected from N, O or S;
R$^3$ is selected from halogen, hydrogen, —CN or —NH$_2$;
both instances of R$^4$ are simultaneously hydrogen or both instances of R$^4$, together with the carbon atom to which they are attached form a carbonyl group; and
R$^5$ is selected from methyl or hydrogen.

In another embodiment, the invention relates to a pharmaceutical composition comprising a compound of Formula I, and at least one pharmaceutically acceptable excipient or carrier. In another embodiment, the invention relates to a pharmaceutical dosage form comprising said pharmaceutical composition.

In another embodiment, the invention relates to a method of treating a disease, health condition or disorder in a subject in need thereof, comprising administering, alone or in combination therapy, a therapeutically effective amount of a compound of Formula I, or a pharmaceutically acceptable composition thereof to the subject; wherein the disease or disorder is one that would benefit from sGC stimulation or from an increase in the concentration of NO and/or cGMP.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, by relevant knowledge of the art.

A compound, such as the compounds of Formula I or other compounds herein disclosed, may be present in its free form (e.g., an amorphous form, or a crystalline form or a polymorph). Under certain conditions, compounds may also form co-forms. As used herein, the term co-form is synonymous with the term multi-component crystalline form. When one of the components in the co-form has clearly transferred or lost a proton, the resulting co-form is referred to as a "salt". The formation of a salt is determined by how large the difference is in the pKas between the partners that form the mixture. For purposes of this disclosure, compounds include their pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I respectively. Certain isotopically-labeled compounds of the present invention (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

As used herein, the terms "appropriate" and "suitable" can be used interchangeably.

As used herein, if more than one instance of a substituent is allowed at one time, then each instance of that substituent is chosen independently in each instance. For example, if a phenyl can be substituted with two instances of $R^{100}$, and $R^{100}$ is selected from halogen and methyl, then that means that each instance of $R^{100}$ is separately selected from halogen or methyl; for instance, one $R^{100}$ may be fluoro and one may be methyl, or both may be chloro, etc.

A group may be substituted with "up to" Z instances of a substituent, wherein "n" is an integer. For instance, if "Z" is 3, then the group can be substituted with 0, 1, 2, or 3 substituents. Unless otherwise specified, each of those "Z" instances are always independently selected.

The term "alkyl" (as in "alkyl chain" or "alkyl group"), as used herein, refers to a saturated linear or branched-chain monovalent hydrocarbon radical. A $C_x$ alkyl is an alkyl chain containing x carbon atoms, wherein x is an integer different from 0. A "$C_{x-y}$ alkyl", wherein x and y are two different integers, both different from 0, is an alkyl chain containing between x and y number of carbon atoms, inclusive. For example, a $C_{1-6}$ alkyl is an alkyl as defined above containing any number between 1 and 6 carbon atoms. Examples of alkyl groups include, but are not limited to, methyl ($C_1$ alkyl), ethyl ($C_2$ alkyl), n-propyl ($C_3$ alkyl), isopropyl $C_3$ alkyl), n-butyl, isobutyl, s-butyl, t-butyl, pentyl, hexyl, heptyl, octyl and the like.

The term "cycloaliphatic" refers to a ring system formed only by carbon and hydrogen atoms and that is fully saturated or that contains one or more units of unsaturation but which is not aromatic In one embodiment, the term "cycloaliphatic" refers to a monocyclic hydrocarbon ring containing 3 to 7 carbons (i.e., a $C_{3-7}$ cycloaliphatic). Suitable cycloaliphatic groups include, but are not limited to, cycloalkyl, cycloalkenyl, and cycloalkynyl. Examples of cycloaliphatic groups include cyclopropyl, cyclobutyl, cyclopentyl, cyclopentenyl, cyclohexyl, cyclohexenyl, cycloheptyl, cycloheptenyl, and the like.

"Cycloalkyl", as used herein, refers to a cycloaliphatic ring system which is completely saturated. In one embodiment, the term "cycloalkyl" refers to a monocyclic 3- to 7-membered saturated cycloaliphatic ring (i.e., a $C_{3-7}$ cycloalkyl). Suitable cycloalkyl groups include, but are not limited to, cyclopropyl, cyclobutyl, cyclopentyl, cyclohexyl, cycloheptyl, and the like.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or $NR^+$ (as in N-substituted pyrrolidinyl).

The term "ring atom" refers to an atom such as C, N, O or S that is part of the ring of a phenyl or a heteroaryl ring. A "substitutable ring atom" is a ring carbon or nitrogen atom bonded to at least one hydrogen atom. The hydrogen can be optionally replaced with a suitable substituent group. "Substitutable ring atom" does not include ring carbon or nitrogen atoms when the structure depicts that they are already attached to one or more moiety other than hydrogen and no hydrogens are available for substitution. When a certain ring, group or chain is optionally substituted, it will be understood that it may be substituted in any or some or all of its substitutable ring atoms.

The term "heterocycle" (as in "heterocyclic ring" or "heterocyclic group"), as used herein, refers to a ring system in which one or more ring atoms are an independently selected heteroatom. Heterocycles are completely saturated or contain one or more units of unsaturation but are not aromatic. In some embodiments, a heterocycle may be a monocyclic ring having 3 to 7 ring atoms (2 to 6 carbon atoms and 1 to 4 heteroatoms). Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl.

As used herein, the terms "halogen" or "halo" mean F, Cl, Br, or I.

The term "haloalkyl" means alkyl substituted with one or more halogen atoms. For example, a $C_{1-3}$ haloalkyl could be —$CFHCH_2CHF_2$.

The term "fluoroalkyl" means alkyl substituted with one or more fluorine atoms. This term includes perfluorinated alkyl groups, such as —$CF_3$ and —$CF_2CF_3$.

As used herein, an "amino" group refers to —$NH_2$.
The term "hydroxyl" or "hydroxy" refers to —OH.
As used herein, a "carbonyl", used alone or in connection with another group refers to —(O)— (a carbon atom bound to oxygen through a double bond) or —C(O)H (if said carbonyl group is situated in the terminal position of a chain).

The compounds of the invention are defined herein by their chemical structures and/or chemical names. Where a compound is referred to by both a chemical structure and a chemical name, and the chemical structure and chemical name conflict, the chemical structure is determinative of the compound's identity.

Substituents $R^n$ are generally defined when introduced and retain that definition throughout the specification and in all independent claims.

Compound Embodiments

In one embodiment, the invention is directed to compounds of Formula I:

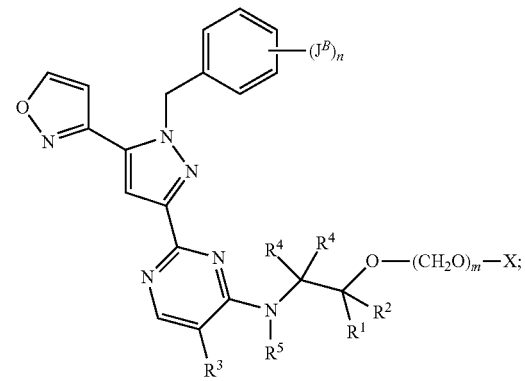

Formula I wherein,

X is selected from —$P(O)(OH)_2$, —$P(O)(OH)O^-$ $M^+$, —$P(O)(O^-)_2(M^+)_2$ or —$P(O)(O^-)_2D^{2+}$; wherein M+ is a pharmaceutically acceptable monovalent cation and $D^{2+}$ is a pharmaceutically acceptable divalent cation;

each $J^B$ is independently selected from halogen;

m is selected from 0 or 1;

n is selected from 0, 1, 2, 3 or 4;

$R^1$ is selected from $C_{1-4}$ alkyl, $C_{1-4}$ fluoroalkyl, —$C(O)NH_2$ or hydrogen; and $R^2$ is selected from $C_{1-4}$ alkyl, $C_{1-4}$ fluoroalkyl or hydrogen; or, alternatively, $R^1$ and $R^2$, together with the carbon atom to which they are attached form an unsubstituted $C_{3-7}$ cycloaliphatic ring or an unsubstituted 3 to 7-membered heterocyclic ring, containing up to 2 heteroatoms independently selected from N, O or S;

$R^3$ is selected from halogen, hydrogen, —CN or —$NH_2$; and both instances of $R^4$ are simultaneously hydrogen or both instances of $R^4$, together with the carbon atom to which they are attached form a carbonyl group; and $R^5$ is selected from hydrogen or methyl.

The compounds of Formula I are phosphate ester prodrugs, and pharmaceutically acceptable salts thereof, of compounds of Formula IA, which are useful as sGC stimulators. For Formula IA, the definitions of $J^B$, n, $R^1$, $R^2$, $R^3$, $R^4$ and $R^5$ are the same as those presented above for Formula I.

Formula IA

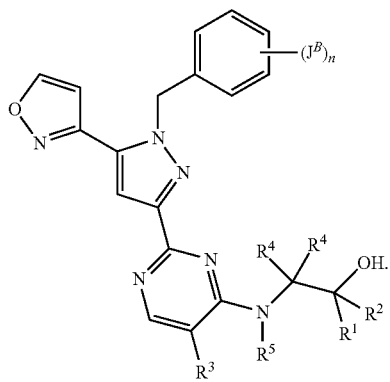

Formula IC

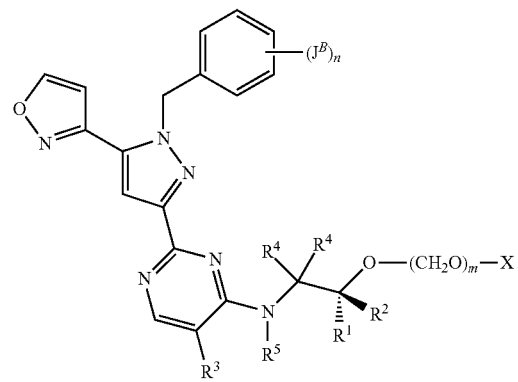

The in vivo biological activity exhibited by compounds of Formula I upon administration is mainly due to the presence of the parent compound of Formula IA that results from cleavage of the prodrug.

The term "prodrug" refers to compounds which are drug precursors which, following administration and absorption, release the drug in vivo via some metabolic, enzymatic, hydrolytic or rapid chemical conversion process. In general, a prodrug possesses less biological activity than the parent compound against the target by itself, before cleavage to the parent drug. A prodrug may improve the physical properties of the parent drug and/or improve overall drug efficacy, for example through the reduction of toxicity and unwanted side effects of a drug by controlling its absorption, blood levels, metabolic distribution and cellular uptake. Prodrugs may also reduce pharmacokinetic inter-subject variability in vivo. A prodrug may also display more desirable pharmaceutical properties and, as such, a prodrug may also improve the formulability of a drug or facilitate the formulability of the drug for certain modes of administration.

The term "parent drug" or "parent compound" refers to the biologically active entity that is released via a metabolic, enzymatic, hydrolytic or rapid chemical conversion process, following administration of the prodrug. In some embodiments, the parent compound may also be the starting material used for the preparation of the prodrug.

The monovalent cations described by $M^+$ comprise $Na^+$, $K^+$ or the monovalent cation of an organic amine.

The divalent cations described by $D^{2+}$ comprise $Ca^{2+}$, $Zn^{2+}$, $Cs^{2+}$, $Mg^{2+}$ or the divalent cation of an organic amine.

In some embodiments of Formula I, wherein $R^1$ and $R^2$ are different, the compounds are those of Formulae IB or IC.

Formula IB

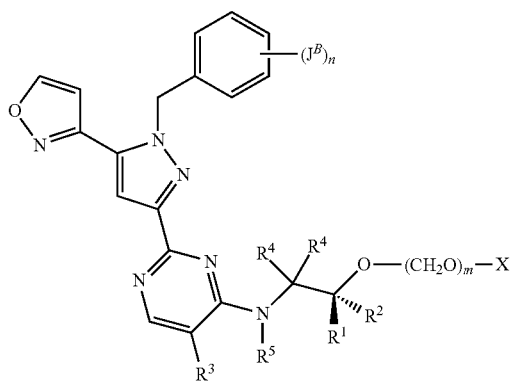

In some embodiments of Formula I, Formula IB or Formula IC, n is selected from 1, 2 or 3. In other embodiments, n is 1 or 2. In other embodiments, n is 1. In still other embodiments, n is 2. In other embodiments, n is 0.

In some embodiments of Formula I, Formula IB or Formula IC, all instances of $J^B$ are fluoro. In other embodiments, all instances of $J^B$ are chloro. In still other embodiments, some instances of $J^B$ are fluoro and some instances of $J^B$ are chloro. In some embodiments, n is 3 and some instances of $J^B$ are chloro and the remaining instances of $J^B$ are fluoro. In other embodiments, n is 3 and all instances of $J^B$ are fluoro. In some embodiments, n is 2 and each $J^B$ is independently selected from fluoro or chloro. In other embodiments, n is 2 and one instance of $J^B$ is chloro and the other instance of $J^B$ is fluoro. In still other embodiments, n is 2 and each $J^B$ is chloro. In yet other embodiments, n is 2 and each $J^B$ is fluoro. In yet other embodiments, n is 1 and $J^B$ is chloro. In yet other embodiments, n is 1 and $J^B$ is fluoro.

In some embodiments of Formula I, both $R^1$ and $R^2$ are simultaneously hydrogen.

In some embodiments of Formula I, Formula IB or Formula IC, $R^1$ is hydrogen and $R^2$ is $C_{1-4}$ alkyl or $C_{1-4}$ fluoroalkyl. In some embodiments, $R^1$ is hydrogen and $R^2$ is $C_{1-2}$ alkyl. In other embodiments, $R^1$ is hydrogen and $R^2$ is methyl. In some embodiments, $R^1$ is hydrogen and $R^2$ is $C_{1-2}$ fluoroalkyl. In other embodiments, $R^1$ is hydrogen and $R^2$ is trifluoromethyl.

In some embodiments of Formula I, both $R^1$ and $R^2$ are simultaneously $C_{1-4}$ alkyl. In some embodiments, they are simultaneously $C_{1-2}$ alkyl. In other embodiments, they are simultaneously methyl.

In some embodiments of Formula I, both $R^1$ and $R^2$ are simultaneously $C_{1-4}$ fluoroalkyl. In some embodiments, they are simultaneously $C_{1-2}$ fluoroalkyl. In other embodiments, they are simultaneously trifluoromethyl.

In some embodiments of Formula I, Formula IB or Formula IC, $R^1$ is —$CONH_2$ and $R^2$ is $C_{1-2}$ alkyl or $C_{1-2}$ fluoroalkyl. In other embodiments, $R^1$ is —$CONH_2$ and $R^2$ is methyl or trifluoromethyl. In still other embodiments, $R^1$ is —$CONH_2$ and $R^2$ is trifluoromethyl.

In some embodiments of Formula I, $R^1$ and $R^2$, together with the carbon atom to which they are attached, form an unsubstituted 3 to 7-membered heterocyclic ring, containing up to 2 heteroatoms independently selected from O or S. In some of these embodiments, $R^1$ and $R^2$, together with the carbon atom to which they are attached, form an unsubstituted 3 to 7-membered heterocyclic ring, containing one ring heteroatom selected from O or S. In other embodiments, said ring heteroatom is O.

In some embodiments of Formula I, Formula IB or Formula IC, m is 1. In other embodiments, m is 0.

In some embodiments of Formula I, Formula IB or Formula IC, both instances of $R^4$ are simultaneously hydrogen. In other embodiments, both instances of $R^4$, together with the carbon atom to which they are attached, form a carbonyl group.

In some embodiments of Formula I, Formula IB or Formula IC, $R^3$ is selected from hydrogen, halogen, —CN or —NH$_2$. In some embodiments, $R^3$ is selected from either hydrogen or halogen. In still other embodiments, $R^3$ is selected from hydrogen, chloro or fluoro. In other embodiments, it is selected from hydrogen or fluoro. In yet other embodiments, it is selected from fluoro or chloro. In other embodiments, $R^3$ is chloro. In other embodiments, $R^3$ is fluoro. In other embodiments, $R^3$ is hydrogen.

In some embodiments of the compounds of Formula I, Formula IB or Formula IC, m is 0 and the compound is one of Formula II, Formula IIB or Formula IIC, respectively, or is a pharmaceutically acceptable salt thereof.

Formula II

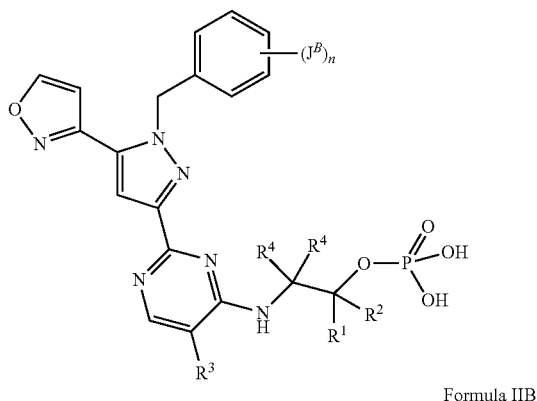

Formula IIB

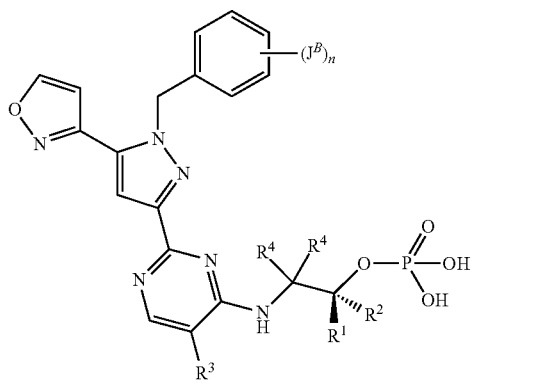

Formula IIC

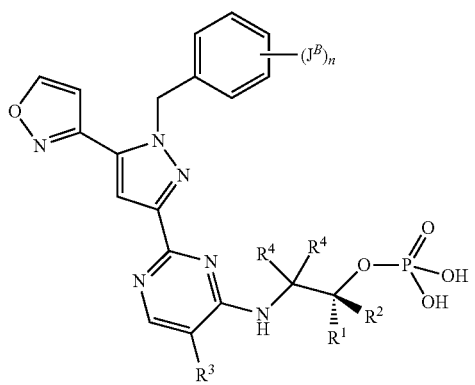

In some embodiments of Formula II, Formula IIB or Formula IIC, n is selected from 1, 2 or 3. In other embodiments, n is 1 or 2. In other embodiments, n is 1. In still other embodiments, n is 2. In other embodiments, n is 0.

In some embodiments of Formula II, Formula IIB or Formula IIC, all instances of $J^B$ are fluoro. In other embodiments, all instances of $J^B$ are chloro. In still other embodiments, some instances of $J^B$ are fluoro and some instances of $J^B$ are chloro. In some embodiments, n is 3 and some instances of $J^B$ are chloro and the remaining instances of $J^B$ are fluoro. In other embodiments, n is 3 and all instances of $J^B$ are fluoro. In some embodiments, n is 2 and each $J^B$ is independently selected from fluoro or chloro. In other embodiments, n is 2 and one instance of $J^B$ is chloro and the other instance of $J^B$ is fluoro. In still other embodiments, n is 2 and each $J^B$ is chloro. In yet other embodiments, n is 2 and each $J^B$ is fluoro. In yet other embodiments, n is 1 and $J^B$ is chloro. In yet other embodiments, n is 1 and $J^B$ is fluoro.

In some embodiments of Formula II, both $R^1$ and $R^2$ are simultaneously hydrogen.

In some embodiments of Formula II, Formula IIB or Formula IIC, $R^1$ is hydrogen and $R^2$ is $C_{1-4}$ alkyl or $C_{1-4}$ fluoroalkyl. In some embodiments, $R^1$ is hydrogen and $R^2$ is $C_{1-2}$ alkyl. In other embodiments, $R^1$ is hydrogen and $R^2$ is methyl. In some embodiments, $R^1$ is hydrogen and $R^2$ is $C_{1-2}$ fluoroalkyl. In other embodiments, $R^1$ is hydrogen and $R^2$ is trifluoromethyl.

In some embodiments of Formula II, both $R^1$ and $R^2$ are simultaneously $C_{1-4}$ alkyl. In some embodiments, they are simultaneously $C_{1-2}$ alkyl. In other embodiments, they are simultaneously methyl.

In some embodiments of Formula II, both $R^1$ and $R^2$ are simultaneously Ca fluoroalkyl. In some embodiments, they are simultaneously $C_{1-2}$ fluoroalkyl. In other embodiments, they are simultaneously trifluoromethyl.

In some embodiments of Formula II, Formula IIB or Formula IIC, $R^1$ is —CONH$_2$ and $R^2$ is $C_{1-2}$ alkyl or $C_{1-2}$ fluoroalkyl. In other embodiments, $R^1$ is —CONH$_2$ and $R^2$ is methyl or trifluoromethyl. In still other embodiments, $R^1$ is —CONH$_2$ and $R^2$ is trifluoromethyl.

In some embodiments of Formula II, $R^1$ and $R^2$, together with the carbon atom to which they are attached, form an unsubstituted 3 to 7-membered heterocyclic ring, containing up to 2 heteroatoms independently selected from O or S. In some of these embodiments, $R^1$ and $R^2$, together with the carbon atom to which they are attached form an unsubstituted 3 to 7-membered heterocyclic ring, containing one ring heteroatom selected from O or S. In other embodiments, said ring heteroatom is O.

In some embodiments of Formula II, Formula IIB or Formula IIC, both instances of $R^4$ are simultaneously hydrogen. In other embodiments, both instances of $R^4$, together with the carbon atom to which they are attached, form a carbonyl group.

In some embodiments of Formula II, Formula IIB or Formula IIC, $R^3$ is selected from hydrogen, halogen, —CN or —NH$_2$. In some of these embodiments, $R^3$ is selected form either hydrogen or halogen.

In still other embodiments, $R^3$ is selected from hydrogen, chloro or fluoro. In other embodiments, it is selected from hydrogen or fluoro. In yet other embodiments, it is selected from fluoro or chloro. In other embodiments, $R^3$ is chloro. In other embodiments, $R^3$ is fluoro. In other embodiments, $R^3$ is hydrogen.

In some embodiments of the compounds of Formula I, Formula IB or Formula IC, m is 1 and the compound is one of Formula III, Formula IIIB or Formula IIIC, respectively, or is a pharmaceutically acceptable salt thereof.

Formula III

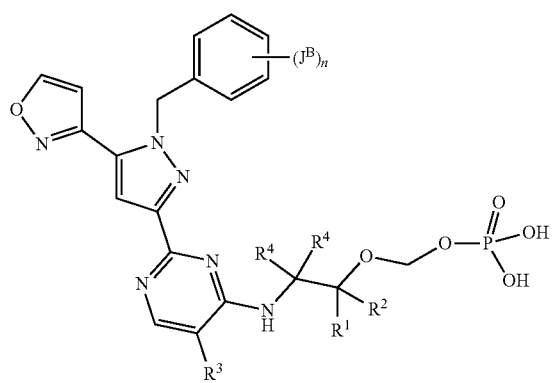

Formula IIIB

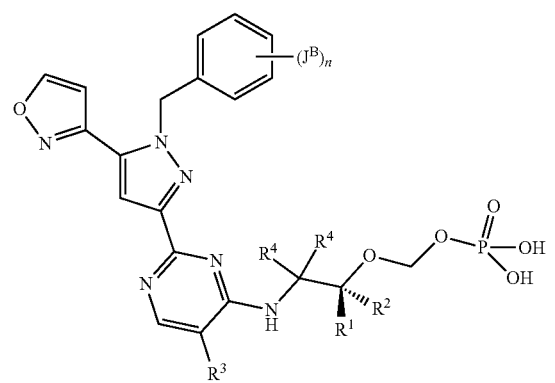

Formula IIIC

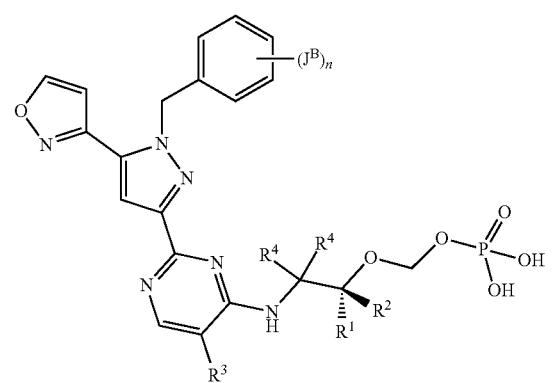

In some embodiments of Formula III, Formula IIIB or Formula IIIC, n is selected from 1, 2 or 3. In other embodiments, n is 1 or 2. In other embodiments, n is 1. In still other embodiments, n is 2. In other embodiments, n is 0.

In some embodiments of Formula III, Formula IIIB or Formula IIIC, all instances of $J^B$ are fluoro. In other embodiments, all instances of $J^B$ are chloro. In still other embodiments, some instances of $J^B$ are fluoro and some instances of $J^B$ are chloro. In some embodiments, n is 3 and some instances of $J^B$ are chloro and the remaining instances of $J^B$ are fluoro. In other embodiments, n is 3 and all instances of $J^B$ are fluoro. In some embodiments, n is 2 and each $J^B$ is independently selected from fluoro or chloro. In other embodiments, n is 2 and one instance of $J^B$ is chloro and the other instance of $J^B$ is fluoro. In still other embodiments, n is 2 and each $J^B$ is chloro. In yet other embodiments, n is 2 and each $J^B$ is fluoro. In yet other embodiments, n is 1 and $J^B$ is chloro. In yet other embodiments, n is 1 and $J^B$ is fluoro.

In some embodiments of Formula III, both $R^1$ and $R^2$ are simultaneously hydrogen.

In some embodiments of Formula III, Formula IIIB or Formula IIIC, $R^1$ is hydrogen and $R^2$ is $C_{1-4}$ alkyl or $C_{1-4}$ fluoroalkyl.

In some embodiments of Formula III, both $R^1$ and $R^2$ are simultaneously $C_{1-4}$ alkyl. In some embodiments, they are simultaneously $C_{1-2}$ alkyl. In other embodiments, they are simultaneously methyl. In some embodiments, $R^1$ is hydrogen and $R^2$ is $C_{1-2}$ alkyl. In other embodiments, $R^1$ is hydrogen and $R^2$ is methyl. In some embodiments, $R^1$ is hydrogen and $R^2$ is $C_{1-2}$ fluoroalkyl. In other embodiments, $R^1$ is hydrogen and $R^2$ is trifluoromethyl.

In some embodiments of Formula III, both $R^1$ and $R^2$ are simultaneously $C_{1-4}$ fluoroalkyl. In some embodiments, they are simultaneously $C_{1-2}$ fluoroalkyl. In other embodiments, they are simultaneously trifluoromethyl.

In some embodiments of Formula III, Formula IIIB or Formula IIIC, $R^1$ is —$CONH_2$ and $R^2$ is $C_{1-2}$ alkyl or $C_{1-2}$ fluoroalkyl. In other embodiments, $R^1$ is —$CONH_2$ and $R^2$ is methyl or trifluoromethyl. In still other embodiments, $R^1$ is —$CONH_2$ and $R^2$ is trifluoromethyl.

In some embodiments of Formula III, $R^1$ and $R^2$, together with the carbon atom to which they are attached form an unsubstituted 3 to 7-membered heterocyclic ring, containing up to 2 heteroatoms independently selected from O or S. In some of these embodiments, $R^1$ and $R^2$, together with the carbon atom to which they are attached, form an unsubstituted 3 to 7-membered heterocyclic ring, containing one ring heteroatom selected from O or S. In other embodiments, said ring heteroatom is O.

In some embodiments of Formula III, Formula IIIB or Formula IIIC, both instances of $R^4$ are simultaneously hydrogen. In other embodiments, both instances of $R^4$, together with the carbon atom to which they are attached, form a carbonyl group.

In some embodiments of Formula III, Formula IIIB or Formula IIIC, $R^3$ is selected from hydrogen, halogen, —CN or —$NH_2$. In some of these embodiments, $R^3$ is selected form either hydrogen or halogen. In still other embodiments, $R^3$ is selected from hydrogen, chloro or fluoro. In other embodiments, it is selected from hydrogen or fluoro. In yet other embodiments, it is selected from fluoro or chloro. In other embodiments, $R^3$ is chloro. In other embodiments, $R^3$ is fluoro. In other embodiments, $R^3$ is hydrogen.

In some embodiments of Formula I, the compound is one of Formula IV, or a pharmaceutically acceptable salt thereof.

Formula IV

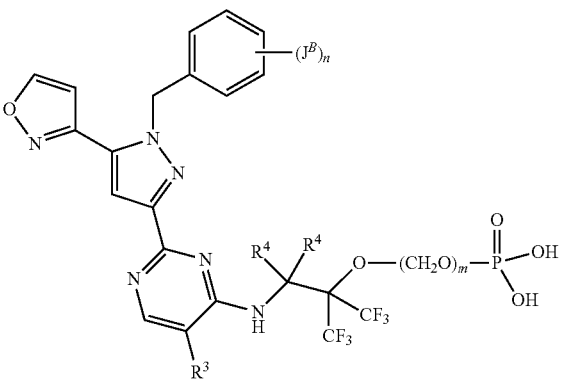

In some embodiments of Formula IV, n is selected from 1, 2 or 3. In other embodiments, n is 1 or 2. In still other embodiments, n is 2. In other embodiments, n is 1. In other embodiments n is 0.

In some embodiments of Formula IV, all instances of $J^B$ are fluoro. In other embodiments, all instances of $J^B$ are chloro. In still other embodiments, some instances of $J^B$ are fluoro and some instances of $J^B$ are chloro. In some embodiments, n is 2 and each $J^B$ is independently selected from fluoro or chloro. In other embodiments, n is 2 and one instance of $J^B$ is chloro and the other instance of $J^B$ is fluoro. In still other embodiments, n is 2 and each $J^B$ is chloro. In yet other embodiments, n is 2 and each $J^B$ is fluoro. In yet other embodiments, n is 1 and $J^B$ is chloro. In yet other embodiments, n is 1 and $J^B$ is fluoro.

In some embodiments of Formula IV, m is 1. In other embodiments, m is 0.

In some embodiments of Formula IV, both instances of $R^4$ are simultaneously hydrogen. In other embodiments, both instances of $R^4$, together with the carbon atom to which they are attached, form a carbonyl group.

In some embodiments of Formula IV, $R^3$ is selected from hydrogen, halogen, —CN or —NH$_2$. In some of these embodiments, $R^3$ is either hydrogen or halogen. In still other embodiments, $R^3$ is selected from hydrogen, chloro or fluoro. In other embodiments, it is selected from hydrogen or fluoro. In yet other embodiments, it is selected from fluoro or chloro. In other embodiments, $R^3$ is chloro. In other embodiments, $R^3$ is fluoro. In other embodiments, $R^3$ is hydrogen.

In some embodiments of Formula IV, the compound is one of Formula V or a pharmaceutically acceptable salt thereof Formula V

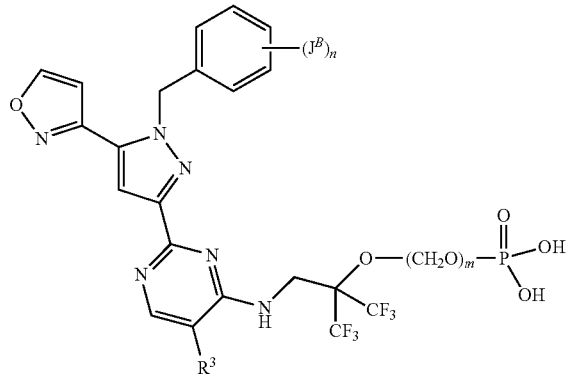

In some embodiments of Formula V, n is selected from 0, 1, 2 or 3. In other embodiments, n is selected from 1 or 2. In other embodiments, n is 1. In still other embodiments, n is 2.

In some embodiments of Formula V, all instances of $J^B$ are fluoro. In other embodiments, all instances of $J^B$ are chloro. In still other embodiments, some instances of $J^B$ are fluoro and some instances of $J^B$ are chloro. In some embodiments, n is 2 and each $J^B$ is independently selected from fluoro or chloro. In other embodiments, n is 2 and one instance of $J^B$ is chloro and the other instance of $J^B$ is fluoro. In still other embodiments, n is 2 and each $J^B$ is chloro. In yet other embodiments, n is 2 and each $J^B$ is fluoro. In yet other embodiments, n is 1 and $J^B$ is chloro. In yet other embodiments, n is 1 and $J^B$ is fluoro.

In some embodiments of Formula V, m is 1. In other embodiments, m is 0.

In some embodiments of Formula V, $R^3$ is selected from hydrogen, halogen, —CN or —NH$_2$. In some of these embodiments, $R^3$ is either hydrogen or halogen. In still other embodiments, $R^3$ is selected from hydrogen, chloro or fluoro. In other embodiments, it is selected from hydrogen or fluoro. In yet other embodiments, it is selected from fluoro or chloro. In other embodiments, $R^3$ is chloro. In other embodiments, $R^3$ is fluoro. In other embodiments, $R^3$ is hydrogen.

In some embodiments of Formula II, the compound is one of Formula VI, or is a pharmaceutically acceptable salt thereof.

Formula VI

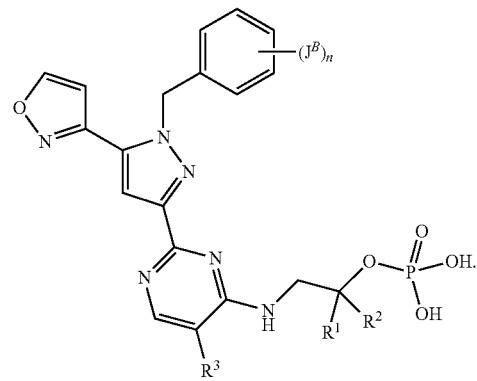

In some embodiments of Formula VI, both $R^1$ and $R^2$ are simultaneously hydrogen. In some embodiments, $R^1$ is hydrogen and $R^2$ is $C_{1-4}$ alkyl or $C_{1-4}$ fluoroalkyl.

In some embodiments of Formula VI, both $R^1$ and $R^2$ are simultaneously $C_{1-4}$ alkyl. In some embodiments, they are simultaneously $C_{1-2}$ alkyl. In other embodiments, they are simultaneously methyl. In some embodiments, $R^1$ is hydrogen and $R^2$ is $C_{1-2}$ alkyl. In other embodiments, $R^1$ is hydrogen and $R^2$ is methyl. In some embodiments, $R^1$ is hydrogen and $R^2$ is $C_{1-2}$ fluoroalkyl. In other embodiments, $R^1$ is hydrogen and $R^2$ is trifluoromethyl.

In some embodiments of Formula VI, both $R^1$ and $R^2$ are simultaneously $C_{1-4}$ fluoroalkyl. In some embodiments, they are simultaneously $C_{1-2}$ fluoroalkyl. In other embodiments, they are simultaneously trifluoromethyl.

In some embodiments of Formula VI, $R^1$ is —CONH$_2$ and $R^2$ is $C_{1-2}$ alkyl or $C_{1-2}$ fluoroalkyl. In other embodiments, $R^1$ is —CONH$_2$ and $R^2$ is methyl or trifluoromethyl. In still other embodiments, $R^1$ is —CONH$_2$ and $R^2$ is trifluoromethyl.

In some embodiments of Formula VI, $R^1$ and $R^2$, together with the carbon atom to which they are attached, form an unsubstituted 3 to 7-membered heterocyclic ring, containing up to 2 heteroatoms independently selected from O or S. In some of these embodiments, $R^1$ and $R^2$, together with the carbon atom to which they are attached form an unsubstituted 3 to 7-membered heterocyclic ring, containing one ring heteroatom selected from O or S. In other embodiments, said ring heteroatom is O.

In some embodiments of Formula VI, wherein $R^1$ and $R^2$ are different, the compound is one of Formula VIA or Formula VIB.

Formula VIA

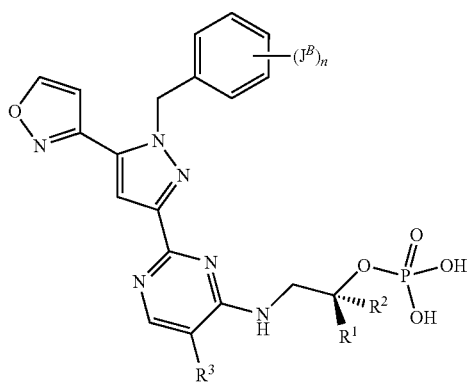

Formula VIB

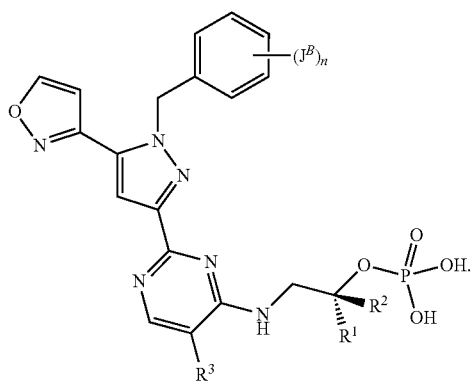

In some embodiments of Formula VI, Formula VIA or Formula VIB, n is selected from 1, 2 or 3. In other embodiments, n is 2. In still other embodiments, n is 1. In still other embodiments n is 3. In yet other embodiments, n is 0.

In some embodiments of Formula VI, Formula VIA or Formula VIB, all instances of $J^B$ are fluoro. In other embodiments, all instances of $J^B$ are chloro. In still other embodiments, some instances of $J^B$ are fluoro and some instances of $J^B$ are chloro. In some embodiments, n is 2 and each $J^B$ is independently selected from fluoro or chloro. In other embodiments, n is 2 and one instance of $J^B$ is chloro and the other instance of $J^B$ is fluoro. In still other embodiments, n is 2 and each $J^B$ is chloro. In yet other embodiments, n is 2 and each $J^B$ is fluoro. In yet other embodiments, n is 1 and $J^B$ is chloro. In yet other embodiments, n is 1 and $J^B$ is fluoro.

In some of the above embodiments of Formula VI, Formula VIA or Formula VIB, $R^3$ is selected from hydrogen, halogen, —CN or —NH$_2$. In some of these embodiments, $R^3$ is either hydrogen or halogen. In still other embodiments, $R^3$ is selected from hydrogen, chloro or fluoro. In other embodiments, it is selected from hydrogen or fluoro. In yet other embodiments, it is selected from fluoro or chloro. In other embodiments, $R^3$ is chloro. In other embodiments, $R^3$ is fluoro. In other embodiments, $R^3$ is hydrogen.

In some embodiments of the any of the above Formulae, the compound is one selected from the Table I, below:

TABLE I

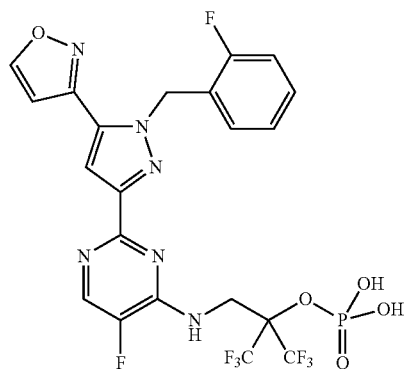 [SMILES: O=P(O)(O)OC(CNc1nc(-c2cc(-c3ccon3)n(Cc3ccccc3F)n2)ncc1F)(C(F)(F)F)C(F)(F)F]

I-1

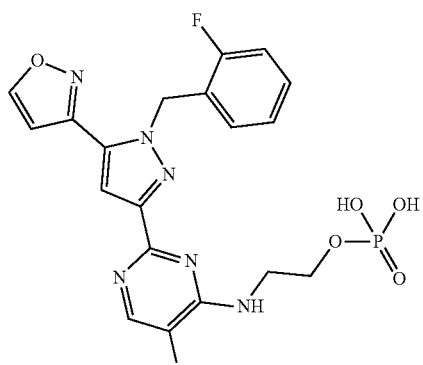

I-2

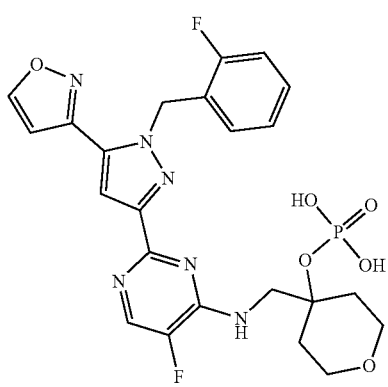 [SMILES: O=P(O)(O)OC1(CNc2nc(-c3cc(-c4ccon4)n(Cc4ccccc4F)n3)ncc2F)CCOCC1]

I-3

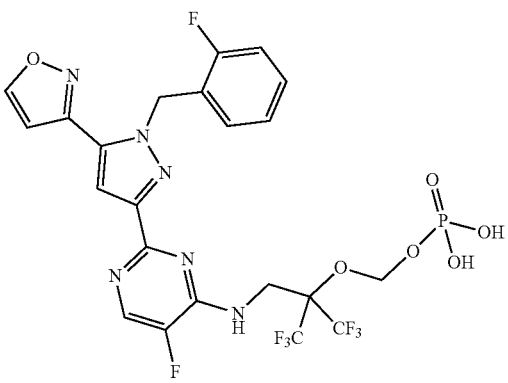 [SMILES: O=P(O)(O)OCOC(CNc1nc(-c2cc(-c3ccon3)n(Cc3ccccc3F)n2)ncc1F)(C(F)(F)F)C(F)(F)F]

I-4

TABLE I-continued

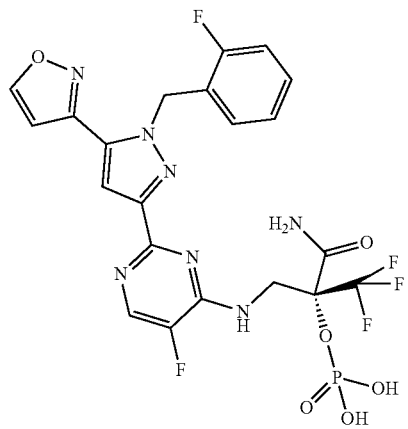 [SMILES: NC(=O)[C@@](CNc1nc(-c2cc(-c3ccon3)n(Cc3ccccc3F)n2)ncc1F)(OP(=O)(O)O)C(F)(F)F]

I-5

In one embodiment of the invention, the compound is I-1. In another embodiment of the invention, the compound is I-2. In another embodiment, the compound is I-3. In still another embodiment, the compound is I-4. In another embodiment, the compound is I-5.

The prodrugs of the present invention are characterized by high aqueous solubility. The aqueous solubility of the prodrugs is much higher than that of the corresponding parent compounds. For instance, the solubility of Compound I-1 is 66-1000 μg/mL at pH 7 and the solubility of Compound I-4 is 71 μg/mL at pH 7; whereas the solubility of the parent compound Intermediate 3 is 2-3 μg/mL at pH 7. Given their improved solubility when compared with the parent compound, the prodrugs of the present invention may be suitable for development of formulations for parenteral delivery, for instance for intravenous delivery, or subcutaneous intramuscular injection, intra-ocular, intrathecal, intracerebral, intracerebroventricular or intra-arterial delivery.

The prodrugs of the present invention are also characterized by rapid cleavage into the parent drug after administration. For instance, they rapidly cleave in an ex-vivo rat intestinal fluid assay. They are also rapidly cleaved in vivo in preclinical animals such as rats and dogs. More specifically, the prodrugs of the present invention are characterized by unexpected short cleavage or release times when administered either in an ex-vivo model system or in vivo in preclinical animals.

Pharmaceutically Acceptable Salts of the Invention.

In all instances described herein, the term "compound" also includes a pharmaceutically acceptable salt of the compound, whether or not the phrase "pharmaceutically acceptable salt" is actually used. The phrase "pharmaceutically acceptable salt," as used herein, refers to pharmaceutically acceptable organic or inorganic salts of a compound of Formula I or Table I. The pharmaceutically acceptable salts of a compound of Formula I or Table I are used in medicine. Salts that are not pharmaceutically acceptable may, however, be useful in the preparation of a compound of Formula I or Table I or of other pharmaceutically acceptable salts. A pharmaceutically acceptable salt involves the inclusion of another atom or molecule acting as the counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. In some instances, the counter ions may be the same. In other instances, they may be different for each charged atom. Hence, a pharmaceutically acceptable salt can have one or more charged atoms and/or one or more counter ions.

Pharmaceutically acceptable salts of the compounds described herein include those derived from the reaction of the compounds of Formula I or Table I with inorganic or organic bases. In some embodiments, the salts can be prepared in situ during the final isolation and purification of the compounds. In other embodiments, the salts can be prepared from the free form of the compound of Formula I or Table I in a separate synthetic step.

For compounds of Formula I or Table I, which contain a phosphoric acid moiety, the term suitable "pharmaceutically acceptable salts" refers to salts prepared from pharmaceutically acceptable non-toxic bases including inorganic bases and organic bases. Salts derived from inorganic bases include salts of aluminum, ammonium, calcium, copper, ferric, ferrous, lithium, magnesium, manganic salts, manganous, potassium, sodium, zinc and the like. Particular embodiments include calcium, magnesium, zinc, cesium, potassium and sodium salts as well as salts of organic amines. Salts derived from pharmaceutically acceptable organic non-toxic amines include salts of primary, secondary and tertiary amines, substituted amines including naturally occurring substituted amines, cyclic amines and basic ion exchange resins, such as arginine, betaine, caffeine, choline, N, N¹-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine, leucine, isoleucine, methionine, alanine, meglumine and the like. A specific embodiment is the meglumine salt.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

Pharmaceutical Compositions and Methods of Administration.

The compounds herein disclosed, and their pharmaceutically acceptable salts thereof, may be formulated as pharmaceutical compositions or "formulations".

A typical formulation is prepared by mixing a compound of Formula I or Table I, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I or Table I, or a pharmaceutically acceptable salt thereof, is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g., enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I or Table I or a pharmaceutically acceptable salt or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Formula I or Table I, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I or Table I or a pharmaceutically acceptable salt thereof is typically formulated into pharmaceutical dosage forms to provide an easily controllable dosage of the drug and to enable patient compliance with the prescribed regimen. Pharmaceutical formulations of a compound of Formula I or Table I, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mlhr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I or Table I, or a pharmaceutically acceptable salt thereof, will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEENM, PLURONICSM or polyethylene glycol (PEG). The active pharmaceutical ingredients may also be entrapped in microcapsules prepared, for example, by coacervation techniques or by interfacial polymerization, e.g., hydroxymethylcelulose or gelatin-microcapsules and poly-(methyl methacrylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g., orally (e.g., using capsules, powders, solutions, suspensions, tablets, sublingual tablets and the like), by inhalation (e.g., with an aerosol, gas, inhaler, nebulizer or the like), to the ear (e.g., using ear drops), topically (e.g., using creams, gels, liniments, lotions, ointments, pastes, transdermal patches, etc.), ophthalmically (e.g., with eye drops, ophthalmic gels, ophthalmic ointments), rectally (e.g., using enemas or suppositories), nasally, buccally, vaginally (e.g., using douches, intrauterine devices, vaginal suppositories, vaginal rings or tablets, etc.), via an implanted reservoir or the like, or parenterally depending on the severity and type of the disease being treated.

The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, subcutaneously or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I or Table I, or a pharmaceutically acceptable salt thereof, that are suitable for oral administration may be prepared as discrete units such as tablets, pills, troches, lozenges, aqueous or oil suspensions, dispersible powders or granules, emulsions, hard or soft capsules, e.g., gelatin capsules, syrups or elixirs. Formulations of a compound intended for oral use may be prepared according to any method known to the art for the manufacture of pharmaceutical compositions.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g., for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol or PEG400. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Formula I or Table I, or a pharmaceutically acceptable salt thereof, in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a compound of Formula I or Table I, or a pharmaceutically acceptable salt thereof, contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUSM model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I or Table I, or a pharmaceutically acceptable salt thereof, may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I or Table I, or a pharmaceutically acceptable salt thereof, include Tween™-60, SpanT™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I or Table I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert or accepted in the veterinary art and are compatible with the active ingredient. These veterinary compositions may be administered parenterally, orally or by any other desired route.

Therapeutic Methods

Increased production of NO or increased concentration of cGMP in a tissue leads to vasodilation, inhibition of platelet aggregation and adhesion, anti-hypertensive effects, anti-remodeling effects, anti-fibrotic, anti-apoptotic effects, anti-inflammatory effects and neuronal signal transmission effects, among other effects.

In another aspect, the invention relates to the treatment of certain disorders by using certain prodrugs of certain sGC stimulators, or their pharmaceutically acceptable salts or pharmaceutical compositions comprising them, either alone or in combination, in a patient in need thereof.

The present disclosure relates to certain prodrugs of stimulators of soluble guanylate cyclase (sGC), pharmaceutically acceptable salts and pharmaceutical formulations thereof and their use, alone or in combination with one or more additional agents, for treating and/or preventing various diseases, wherein an increase in the concentration of NO or an increase in the concentration of cGMP might be desirable.

In other embodiments, the compounds here disclosed are prodrugs of sGC stimulators that may be useful in the prevention and/or treatment of diseases and disorders characterized by undesirable reduced bioavailability of and/or sensitivity to NO in a biological system (e.g., in the human body), such as those associated with conditions of oxidative stress or nitrosative stress.

The term "cardiovascular disease" (or "cardiovascular disorder") as used herein, refers to a disease based on the abnormal symptoms of circulatory organs such as the heart, blood vessels (arteries, capillaries, and veins) or both. The term also includes any disease that affects the cardiovascular system in general, including cardiac disease, vascular diseases of the brain, vascular diseases of the kidney, liver and associated organs, or lung, and peripheral arterial disease, among others.

A "sGC-related cardiovascular disease" is one for which the NO/sGC/cGMP system is known or suspected to be involved and is a cardiovascular disease that can be treated or prevented by sGC activation/stimulation, by activation of a NO synthase, or by addition of NO or an NO-donor or an NO precursor such as L-Arginine or L-citruline, or by inhibition of a PDE (phosphodiesterase) enzyme responsible for the breakdown of cGMP, or a combination of the any of the above methods.

The term "vasodilation" as used herein, refers to the widening of blood vessels. It results from relaxation of smooth muscle cells within the vessel walls, in particular in the large veins, large arteries, and smaller arterioles. In essence, the process is the opposite of "vasoconstriction", which is the narrowing of blood vessels. When blood vessels dilate, the flow of blood is increased due to a decrease in vascular resistance. Therefore, dilation of arterial blood vessels (mainly the arterioles) decreases blood pressure. The response may be intrinsic (due to local processes in the surrounding tissue) or extrinsic (due to hormones or the nervous system). In addition, the response may be localized to a specific organ (depending on the metabolic needs of a particular tissue, as during strenuous exercise), or it may be systemic (seen throughout the entire systemic circulation).

The term "vasoconstriction" as used herein refers to the narrowing of a blood vessel due to muscle contraction. Vasoconstriction is one mechanism by which the body regulates and maintains mean arterial pressure (MAP). Generalized vasoconstriction usually results in an increase in systemic blood pressure, but it may also occur in specific tissues, causing a localized reduction in blood flow.

As used herein, the term "bronchoconstriction" is used to define the constriction of the airways in the lungs due to the tightening of surrounding smooth muscle, with consequent coughing, wheezing, and shortness of breath. The condition has a number of causes, the most common being asthma. Exercise and allergies can bring on the symptoms in an otherwise asymptomatic individual. Other conditions such as chronic obstructive pulmonary disease (COPD) can also present with bronchoconstriction.

Throughout this disclosure, the terms "hypertension", "arterial hypertension" or "high blood pressure (HBP)" are used interchangeably and refer to an extremely common and highly preventable chronic condition in which blood pressure (BP) in the arteries is higher than normal or desired. If not properly controlled, it represents a significant risk factor for several serious cardiovascular and renal conditions. Hypertension may be a primary disease, called "essential hypertension" or "idiopathic hypertension", or it may be caused by or related to other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension. Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

The term "coronary artery disease" refers to a condition in which the blood supply to the heart muscle is partially or completely blocked (ischemia of the heart muscle or myocardium). This reduced blood supply to the myocardium may result in a number of "acute myocardial syndromes": chest pain ("angina", also called "angina pectoris", stable or unstable) and different types of heart attacks ("myocardial infarction" or MI). One common cause of coronary artery disease is "atherosclerosis" which refers to hardening of the arteries, due to fatty deposits in the artery walls which then may progress through formation of atherosclerotic plaques, to narrowing and eventually blockage of blood flow to the in the artery. This process of atherosclerosis may affect other arteries as well, not just those of the heart. A blood clot is the most common cause of the blockage of the artery, as usually the artery is already partially blocked due to atherosclerotic plaque (atheroma); the atheroma may rupture or tear, leading to the formation of a clot. Occasionally, coronary artery disease is caused by spasm of a coronary artery, which can occur spontaneously or as a result of the use of certain drugs (e.g., cocaine, nicotine). Rarely, the cause of coronary artery disease is a birth defect, a viral infection (e.g., Kawasaki disease), systemic lupus erythematosus (lupus), inflammation of the arteries (arteritis), a blood clot that travelled from a heart chamber into one of the coronary arteries or physical damage (e.g., from injury or radiation therapy).

"Unstable angina", as used herein, refers to a change in the pattern of angina symptoms including prolonged or worsening angina and new onset of severe symptoms.

MI (myocardial infarction) can be classified into two types: "Non-ST-segment elevation" MI and "ST-segment elevation" MI. The complications of acute coronary syndromes depend on how much, how long, and where the coronary artery is blocked. If the blockage affects a large amount of heart muscle, the heart will not pump effectively. If the blockage shuts off blood flow to the electrical system of the heart, the heart rhythm may be affected. When a heart attack occurs, part of the myocardium dies. Dead tissue and the scar tissue that replaces it, does not contract. The scar tissue sometimes even expands or bulges when the rest of the heart tries to contract. Consequently, there is less muscle to pump blood. If enough muscle dies, the heart's pumping ability may be so reduced that the heart cannot meet the body's demands for oxygen and blood. Heart failure, low blood pressure or both then develop. If more than half of the myocardium is damaged or dies, the heart generally cannot function and severe disability or death is likely.

As used herein "Heart Failure" (HF) is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neuro-hormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness; edema of the feet, ankles and legs; rapid weight gain; or chronic cough, including that producing mucus or blood. Depending on its clinical presentation, heart failure is classified as de novo, transient, acute, post-acute or chronic. Acute heart failure, i.e., the rapid or gradual onset of symptoms requiring urgent therapy, may develop de novo or as a result of chronic heart failure becoming decompensated. The term "Heart failure" is often used to mean "chronic heart failure". The terms "congestive heart failure (CHF)" or "congestive cardiac failure (CCF)" are often used interchangeably with chronic heart failure. Common causes of heart failure include coronary artery disease including a previous myocardial infarction (heart attack), high blood pressure, atrial fibrillation, valvular heart disease, and cardiomyopathy. These cause heart failure, by changing either the structure or the functioning of the heart.

There are two main types of heart failure: "heart failure due to reduced ejection fraction (HFREF)", also known as "heart failure due to left ventricular systolic dysfunction" or "systolic heart failure", and "heart failure with preserved ejection fraction (HFPEF)", also known as "diastolic heart failure" or "heart failure with normal ejection fraction (HFNEF)". Ejection fraction is the proportion of blood in the heart pumped out of the heart during a single contraction. It is a percentage with normal being between 50 and 75%.

The term "acute" (as in "acute HF") is used to mean rapid onset, and "chronic" refers to long duration. Chronic heart failure is a long term situation, usually with stable treated symptomatology. "Acute decompensated" heart failure is worsening or decompensated heart failure, referring to episodes in which a person can be characterized as having a change in heart failure signs and symptoms resulting in a need for urgent therapy or hospitalization. Heart failure may also occur in situations of high output (then it is termed "high output cardiac failure") where the ventricular systolic function is normal but the heart cannot deal with an important augmentation of blood volume.

In cardiovascular physiology, the term "Ejection Fraction (EF)" is defined as the fraction of blood in the left and right ventricles that is pumped out with each heartbeat or cardiac cycle. In finite mathematics allowed by medical imaging, EF is applied to both the right ventricle, which ejects blood via the pulmonary valve into the pulmonary circulation, or the left ventricle, which ejects blood via the aortic valve into the cerebral and systemic circulation.

The term "heart failure with preserved ejection fraction (HFPEF)" is commonly understood to refer to a manifestation of signs and symptoms of heart failure with an ejection fraction greater than 55%. It is characterized by a decrease in left ventricular compliance, leading to increased pressure in the left ventricle. Increased left atrial size is often seen with HFPEF as a result of the poor left ventricular function. There is an increased risk for congestive heart failure, atrial fibrillation, and pulmonary hypertension. Risk factors are hypertension, hyperlipidemia, diabetes, smoking, and obstructive sleep apnea. In this type of heart failure, the heart muscle contracts well but the ventricle does not fill with blood well in the relaxation phase.

The term "heart failure with reduced ejection fraction (HFREF)" refers to heart failure in which the ejection fraction is less than 40%.

Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, non-voluntary loss of at least 6% of body weight over a period of six months.

The term "arrhythmias", as used herein, refers to abnormal heart rhythms that occur in more than 90% of people who have had a heart attack. Sometimes the problem is with the part of the heart that triggers the heartbeat and the heart rate may be too slow, other times the problems may cause the heart to beat too rapidly or irregularly. Sometimes the signal to beat is not conducted from one part of the heart to the other and the heartbeat may slow or stop. In addition, areas of the myocardium that have not died but have poor blood flow may be irritable. This causes heart rhythm problems such as ventricular tachycardia or ventricular fibrillation. This may lead to cardiac arrest if the heart stops pumping entirely.

The "pericardium" is the sack or membrane that surrounds the heart. "Pericarditis" or inflammation of this membrane may develop as a result of a heart attack and may result in fever, pericardial effusion, inflammation of the membranes covering the lungs (pleura), pleural effusion, and joint pain. Other complications after a heart attack may include malfunction of the mitral valve, rupture of the heart muscle, a bulge in the wall of the ventricle (ventricular aneurysm), blood clots, and low blood pressure.

The term "cardiomyopathy" refers to the progressive impairment of the structure and function of the muscular walls of the heart chambers. The main types of cardiomyopathies are dilated, hypertrophic and restrictive. Cardiomyopathies often cause symptoms of heart failure, and they may also cause chest pain, fainting and sudden death.

The terms "mitral valve regurgitation", "mitral regurgitation", "mitral insufficiency" or "mitral incompetence" refer to a situation in which the mitral valve of the heart doesn't close tightly, allowing blood to flow backward in the heart. As a result, blood can't move through the heart or to the rest of the body as efficiently, resulting in fatigue or shortness of breath.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertriglyceridemia" involves elevated levels of triglycerides). "Hyperlipoproteinemia" refers to elevated levels of lipoproteins (usually LDL unless otherwise specified).

The term "steatosis" refers to the abnormal retention of lipids within a cell. It usually reflects an impairment of the normal processes of synthesis and elimination of triglycerides. Excess fat accumulates in vesicles that displace the cytoplasm of the cell. In severe cases the cell may burst. Usually steatosis is observed in the liver as it is the organ mostly associated with fat metabolism. It can also be observed in the heart, kidneys and muscle tissue.

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or the brain. PVD can result from atherosclerosis, inflammatory processes leading to stenosis, an embolism, thrombus formation or other types of occlusions. It causes either acute or chronic "ischemia (lack of blood supply)". Often PVD is a term used to refer to atherosclerotic blockages found in the lower extremity. PVD also includes a subset of diseases classified as microvascular diseases resulting from episodic narrowing of the arteries (e.g., "Raynaud's phenomenon"), or widening thereof (erythromelalgia), i.e., vascular spasms. Peripheral arterial diseases include occlusive thrombotic vasculitis, peripheral arterial occlusive disease, Raynaud's disease, and Raynaud's syndrome. Common symptoms are cold leg or feet, intermittent claudication, lower limb pain and critical limb ischemia (lower limb ulcers and necrosis). Diagnosis and treatment guidelines for peripheral arterial disease can be found in Eur. J. Vasco Endovasc. Surg, 2007, 33(1), Sl.

The term "stenosis" as used herein refers to an abnormal narrowing in a blood vessel or other tubular organ or structure. It is also sometimes called a "stricture" (as in urethral stricture). The term "coarctation" is a synonym, but is commonly used only in the context of aortic coarctation. The term "restenosis" refers to the recurrence of stenosis after a procedure.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin. The material that forms the embolism can have a number of different origins: if the material is blood the "embolus" is termed a "thrombus"; the solid material could also comprise fat, bacterial remains, infected tissue, etc.

"Ischemia" is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism). If the "ischemia" takes place in the heart muscle (or "myocardium") the ischemia is termed myocardial ischemia. Other types of ischemia are for instance cerebral ischemia, critical limb ischemia and the like.

"Reperfusion" occurs when blood supply returns to the tissue after a period of ischemia. Upon restoration of circulation to the tissue, inflammatory and oxidative stress processes may develop. One example of this chain of events is ischemia-reperfusion associated with organ transplants.

"Reperfusion injury" is the tissue damage caused when blood supply returns to the tissue after a period of ischemia and inflammation and oxidative damage ensue rather than restoration of normal function. Reperfusion of ischemic issues is often associated with microvascular injury, particularly due to the increased permeability of capillaries and arterioles that lead to an increase in diffusion and fluid filtration across the tissues. The activated endothelial cells produce more reactive oxygen species but less NO following reperfusion, and the imbalance results in an inflammatory response. White blood cells, carried to the area by the newly returned blood flow, release a host of inflammatory factors and free radicals in response to tissue damage. The restored blood flow brings with it oxygen that damages cellular proteins, DNA and plasma membranes. This process of ischemia-reperfusion is also thought to be responsible for formation and failure to heal of chronic wounds, (e.g., pressure sores or diabetic ulcers).

The term "angiopathy" as used herein is the generic term for a disease of the blood vessels (arteries, veins, and capillaries). The most common and most prevalent angiopathy is "diabetic angiopathy", a common complication of chronic diabetes. Another common type of angiopathy is "cerebral amyloid angiopathy" (CAA), also known as congophilic angiopathy, wherein amyloid deposits form in the walls of the blood vessels of the central nervous system. The term congophilic is used because the presence of the abnormal aggregations of amyloid can be demonstrated by microscopic examination of brain tissue after application of a special stain called Congo red. The amyloid material is only found in the brain and as such the disease is not related to other forms of amyloidosis.

A "stroke", or cerebrovascular accident (CVA), is the rapid loss of brain function(s) due to disturbance in the blood supply to the brain. This can be due to "ischemia" (lack of blood flow with resultant insufficient oxygen and glucose supply to the tissue) caused by blockage (thrombosis, arterial embolism, fat accumulation or a spasm), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Vascular dementia" is the 2nd most common cause of dementia among the elderly. It is more common among men and usually begins after age 70. It occurs more often in people who have vascular risk factors (e.g., hypertension, diabetes mellitus, hyperlipidemia, smoking) and in those who have had several strokes. Many people have both vascular dementia and Alzheimer disease. Vascular dementia typically occurs when multiple small cerebral infarcts (or sometimes hemorrhages) cause enough neuronal or axonal loss to impair brain function. Vascular dementias include the following types: multiple lacunar infarction (wherein small blood vessels are affected and infarcts occur deep within hemispheric white and gray matter); multi-infarct dementia (wherein medium-sized blood vessels are affected); strategic single-infarct dementia (wherein a single infarct occurs in a crucial area of the brain such as the angular gyrus or the thalamus; Binswanger dementia or subcortical arteriosclerotic encephalopathy (wherein small-vessel dementia is associated with severe, poorly controlled hypertension and systemic vascular disease and which causes diffuse and irregular loss of axons and myelin with widespread gliosis, tissue death due to an infarction, or loss of blood supply to the white matter of the brain).

The term "glioma" refers to a type of tumor that starts in the brain or spine. It is called a glioma because it arises from glial cells. The most common site of gliomas is the brain. Gliomas make up about 30% of all brain and central nervous system tumors and 80% of all malignant brain tumors.

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

In one embodiment, compounds of Formula I or Table I, or pharmaceutically acceptable salts thereof, that are stimulators of sGC, and their pharmaceutically acceptable salts thereof, are therefore useful in the prevention and/or treatment of the following types of cardiac, pulmonary, peripheral, hepatic, kidney, or cerebral vascular/endothelial disorders, conditions and diseases related to circulation:

disorders related to high blood pressure and decreased coronary blood flow; increased acute and chronic coronary blood pressure; arterial hypertension; vascular disorder resulting from cardiac and renal complications; vascular disorders resulting from heart disease, stroke, cerebral ischemia or renal failure; resistant hypertension; diabetic hypertension; essential hypertension; secondary hypertension; gestational hypertension; pre-eclampsia; portal hypertension; myocardial infarction;

heart failure, HFPEF, HFREF; acute and chronic HF; more specific forms of HF: acute decompensated HF, right ventricular failure, left ventricular failure, total HF, ischemic cardiomyopathy, dilated cardiomyopathy, congenital heart defects, HF with valvular defects, mitral valve stenosis, mitral valve insufficiency, aortic valve stenosis, aortic valve insufficiency, tricuspid stenosis, tricuspic insufficiency, pulmonary valve stenosis, pulmonary valve insufficiency, combined valvular defects; diabetic heart failure; alcoholic cardiomyopathy or storage cardiomyopathies; diastolic HF, systolic HF; acute phases of an existing chronic HF (worsening HF); diastolic or systolic dysfunction; coronary insufficiency; arrhythmias; reduction of ventricular preload; cardiac hypertrophy; heart failure/cardiorenal syndrome; portal hypertension; endothelial dysfunction or injury; disturbances of atrial and ventricular rhythm and conduction disturbances: atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia; Wolff-Parkinson-White syndrome or acute coronary syndrome; Boxer cardiomyopathy; premature ventricular contraction; cardiomyopathy; cancer-induced cardiomyopathy; chemotherapy-induced cardiotoxicity;

thromboembolic disorders and ischemias; myocardial ischemia; infarction; myocardial infarction; heart attack; myocardial insufficiency; endothelial dysfunction; stroke; transient ischemic attacks (TIAs); obstructive thromboanginitis; stable or unstable angina pectoris; coronary spasms or spasms of the peripheral arteries; variant angina; Prinzmetal's angina; cardiac hypertrophy; preeclampsia; thrombogenic disorders; ischemia-reperfusion damage; ischemia-reperfusion associated with organ transplant; ischemia-reperfusion associated with lung transplant, pulmonary transplant, cardiac transplant, venous graft failure; conserving blood substituents in trauma patients;

peripheral vascular disease; peripheral arterial disease; peripheral occlusive arterial disease; hypertonia; Raynaud's syndrome or phenomenon (primary and secondary); Raynaud's disease; critical limb ischemia; peripheral embolism; intermittent claudication; vasoocclusive crisis; muscular dystrophy, Duchenne muscular dystrophy, Becker muscular dystrophy; microcirculation abnormalities; control of vascular leakage or permeability; lumbar spinal canal stenosis; occlusive thrombotic vasculitis; thrombotic vasculitis; peripheral perfusion disturbances; arterial and venous thrombosis; microalbuminuria; peripheral and autonomic neuropathies; diabetic neuropathic pain; diabetic microangiopathies; hepatic vasoocclusive disorder; vasoocclusive crisis in sickle cell disease; hypertensive crisis;

edema; renal edema due to heart failure;

Alzheimer's disease; Parkinson's disease; vascular dementias; vascular cognitive impairment; cerebral vasospasm; congenital myasthenic syndrome; subarachnoid hemorrhage; traumatic brain injury; improving perception, capacity for concentration, capacity for learning or memory performance after cognitive disturbances such as those ocurring in mild cognitive impairment, age-related learning and memory disturbances, age-related memory loss, vascular dementia, head injury, stroke, post-stroke dementia, post-traumatic head injury, general disturbances of concentration and disturbances of concentration in children with learning and memory problems; Lewy body dementia; dementia with frontal lobe degeneration including Pick's syndrome; progressive nuclear palsy; dementia with corticobasal degeneration; Amyotrophic Lateral Sclerosis (ALS); Huntington's disease; demyelination; Multiple Sclerosis; thalamic degeneration; Creutzfeldt-Jakob dementia; HIV-dementia; schizophrenia with dementia or Korsakoff psychosis; Multiple System Atrophy and other forms of Parkinsonism Plus; movement disorders; neuroprotection; anxiety, tension and depression or post-traumatic stress disorder (PTSD); bipolar disorder; schizophrenia; CNS-related sexual dysfunction and sleep disturbances; pathological eating disorders and use of luxury foods and addictive drugs; controlling cerebral perfusion; migraines; prophylaxis and control of consequences of cerebral infarction (apoplexia cerebri); prophylaxis and control of consequences of stroke, cerebral ischemias and head injury; neuropathies associated to a CNS disease; neuropathic pain neuropathic pain associated with MS; chemotherapy induced neuropathic pain; neuropathic pain associated with shingles; neuropathic pain associated with spine surgery;

shock; cardiogenic shock; sepsis; septic shock; anaphylactic shock; aneurysm; control of leukocyte activation; inhibition or modulation of platelet aggregation; multiple organ dysfunction syndrome (MODS); multiple organ failure (MOF);

pulmonary/respiratory conditions: pulmonary hypertension (PH); pulmonary arterial hypertension (PAH), and associated pulmonary vascular remodeling; vascular remodeling in the form of localized thrombosis and right heart hypertrophy; pulmonary hypertonia; primary pulmonary hypertension; secondary pulmonary hypertension; familial pulmonary hypertension; sporadic pulmonary hypertension; pre-capillary pulmonary hypertension; idiopathic pulmonary hypertension; other forms of PH; PH associated with left ventricular disease, HIV, SCD, thromboembolism (CTEPH), sarcoidosis, COPD, pulmonary fibrosis, acute respiratory distress syndrome (ARDS), acute lung injury, alpha-antitrypsin deficiency (AATD), pulmonary emphysema, smoking-induced emphysema and cystic fibrosis (CF); thrombotic pulmonary arteriopathy; plexogenic pulmonary arteriopathy; cystic fibrosis; bronchoconstriction or pulmonary bronchoconstriction; acute respiratory syndrome; lung fibrosis, lung transplant; asthmatic diseases;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism; pulmonary embolism due to tumor, parasites or foreign material; connective tissue disease, lupus, lupus nephritis, schistosomiasis, sarcoidosis, chronic obstructive pulmonary disease, asthma, emphysema, chronic bronchitis, pulmonary capillary hemangiomatosis, histiocytosis X, lymphangiomatosis, compressed pulmonary vessels; compressed pulmonary vessels due to adenopathy, tumor or fibrosing mediastinitis;

arterosclerotic diseases or conditions: atherosclerosis; atherosclerosis associated with endothelial injury, platelet and monocyte adhesion and aggregation, smooth muscle proliferation or migration; restenosis; restenosis developed after thrombolysis therapies, percutaneous transluminal angioplasties (PTAs), transluminal coronary angioplasties (PTCAs), heart transplant, bypass operations or inflammatory processes;

micro and macrovascular damage (vasculitis); increased levels of fibrinogen and low density DLD; increased concentration of plasminogen activator inhibitor 1 (PA-1);

metabolic syndrome; metabolic diseases or diseases associated with metabolic syndrome: obesity; excessive subcutaneous fat; excessive adiposity; diabetes; high blood pressure; lipid related disorders, hyperlipidemias, dyslipidemia, hypercholesterolemias, decreased high-density lipoprotein cholesterol (HDL-cholesterol), moderately elevated low-density lipoprotein cholesterol (LDL-cholesterol) levels, hypertriglyceridemias, hyperglyceridemia, hypolipoproteinanemias, sitosterolemia, fatty liver disease, alcoholic fatty liver disease (AFLD), non-alcoholic fatty liver disease (NAFLD), hepatitis; preeclampsia; polycystic kidney disease progression; liver steatosis or abnormal lipid accumulation in the liver, non-alcoholic steatohepatitis (NASH); steatosis of the heart, kidneys or muscle; alphabetalipoproteinemia; sitosterolemia; xanthomatosis; Tangier disease; hyperammonemia and related diseases; hepatic encephalopathies; other toxic encephalopathies; Reye syndrome;

sexual, gynecological and urological disorders of conditions: erectile dysfunction; impotence; premature ejaculation; female sexual dysfunction; female sexual arousal dysfunction; hypoactive sexual arousal disorder; vaginal atrophy; dyspaneuria; atrophic vaginitis; benign prostatic hyperplasia (BPH), prostatic hypertrophy, prostatic enlargement; bladder outlet obstruction; bladder pain syndrome (BPS); interstitial cystitis (IC); overactive bladder; neurogenic bladder and incontinence; diabetic nephropathy; primary and secondary dysmenorrhea; lower urinary tract syndromes (LUTS); endometriosis; pelvic pains; benign and malignant diseases of the organs of the male and female urogenital system;

chronic kidney disease; acute and chronic renal insufficiency; acute and chronic renal failure; lupus nephritis; underlying or related kidney diseases: hypoperfusion, intradialytic hypotension, obstructive uropathy, glomerulopathies, glomerulonephritis, acute glomerulonephritis, glomerulosclerosis, tubulointerstitial diseases, nephropathic diseases, primary and congenital kidney diseases, nephritis; diseases characterized by abnormally reduced creatinine and or water excretion; diseases characterized by abnormally increased blood concentrations of urea, nitrogen, potassium and/or creatinine; diseases characterized by altered activity of renal enzymes, diseases characterized by altered activity of glutamyl synthetase; diseases characterized by altered urine osmolarity or urine volume; diseases characterized by increased microalbuminuria, diseases characterized by macroalbuminuria; diseases characterized by lesions of glomeruli and arterioles, tubular dilatation, hyperphosphatemia and/or need for dialysis; sequelae of renal insufficiency; renal-insufficiency related pulmonary enema; renal-insufficiency related to HF; renal insufficiency related to uremia or anemia; electrolyte disturbances (herkalemia, hyponatremia); disturbances of bone and carbohydrate metabolism; acute kidney injury;

ocular diseases or disorders such as glaucoma, retinopathy and diabetic retinopathy.

The term "Inflammation" refers to the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even though the two are often correlated (the former often being a result of the latter). Inflammation can also occur in the absence of infection, although such types of inflammation are usually maladaptive (such as in atherosclerosis). Inflammation is a stereotyped response, and therefore it is considered as a mechanism of innate immunity, as compared to adaptive immunity, which is specific for each pathogen. Progressive destruction of tissue in the absence of inflammation would compromise the survival of the organism. On the other hand, chronic inflammation might lead to a host of diseases, such as hay fever, periodontitis, atherosclerosis, rheumatoid arthritis, and even cancer (e.g., gallbladder carcinoma). It is for that reason that inflammation is normally closely regulated by the body. Inflammation can be classified as either acute or chronic. "Acute inflammation" is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as "chronic inflammation", leads to a progressive shift in the type of cells present at the site of inflammation and is characterized by simultaneous destruction and healing of the tissue from the inflammatory process.

In another embodiment, compounds of Formula I or Table I, or pharmaceutically acceptable salts thereof, that are stimulators of sGC, and their pharmaceutically acceptable salts thereof, are therefore useful in the prevention and/or treatment of the following types of cardiac, pulmonary, peripheral, hepatic, kidney, digestive or Central Nervous System disorders, conditions and diseases which may involve inflammation or an inflammatory process:

heart muscle inflammation (myocarditis); chronic myocarditis; acute myocarditis; viral myocarditis;

vasculitis; pancreatitis; peritonitis; rheumatoid diseases;

inflammatory disease of the kidney; immunological kidney diseases: kidney transplant rejection, immune complex-induced kidney disease, nephropathy induced by toxins, contrast medium-induced nephropathy; diabetic and non-diabetic nephropathy, pyelonephritis, renal cysts, nephrosclerosis, hypertensive nephrosclerosis and nephrotic syndrome;

chronic interstitial inflammations. inflammatory bowel diseases (IBD), Crohn's, Ulcerative Colitis (UC);

inflammatory skin diseases;

inflammatory diseases of the eye, blepharitis, dry eye syndrome, and Sjögren's Syndrome; eye fibrosis.

The term "wound healing" refers to the intricate process where the skin (or another organ or tissue) repairs itself after injury. For instance, in normal skin, the epidermis (outermost layer) and dermis (inner or deeper layer) exist in a steady-state equilibrium, forming a protective barrier against the external environment. Once the protective barrier is broken, the normal (physiologic) process of wound healing is immediately set in motion. The classic model of wound healing is divided into three or four sequential, yet overlapping, phases: (1) hemostasis (not considered a phase by some authors), (2) inflammation, (3) proliferation and (4) remodeling. Upon injury to the skin, a set of complex biochemical events takes place in a closely orchestrated cascade to repair the damage. Within the first few minutes after the injury, platelets adhere to the site of injury, become activated, and aggregate (join together), followed by activation of the coagulation cascade which forms a clot of aggregated platelets in a mesh of cross-linked fibrin protein. This clot stops active bleeding ("hemostasis"). During the inflammation phase, bacteria and cell debris are phagocytosed and removed from the wound by white blood cells. Platelet-derived growth factors (stored in the alpha granules of the platelets) are released into the wound that cause the migration and division of cells during the proliferative phase. The proliferation phase is characterized by angiogenesis, collagen deposition, granulation tissue formation, epithelialization, and wound contraction. In "angiogenesis", vascular endothelial cells form new blood vessels. In "fibroplasia" and granulation tissue formation, fibroblasts grow and form a new, provisional extracellular matrix (ECM) by excreting collagen and fibronectin. Concurrently, "re-epithelialization" of the epidermis occurs, in which epithelial cells proliferate and 'crawl' atop the wound bed, providing cover for the new tissue. During wound contraction, myofibroblasts decrease the size of the wound by gripping the wound edges and contracting using a mechanism that resembles that in smooth muscle cells. When the cells' roles are close to complete, unneeded cells undergo apoptosis. During maturation and remodeling, collagen is remodeled and realigned along tension lines, and cells that are no longer needed are removed by apoptosis. However, this process is not only complex but fragile, and is susceptible to interruption or failure leading to the formation of non-healing chronic wounds (one example includes diabetic wounds or ulcers, and, in particular, diabetic foot ulcers). Factors that contribute to non-healing chronic wounds are diabetes, venous or arterial disease, infection, and metabolic deficiencies of old age.

The terms "bone healing", or "fracture healing" refers to a proliferative physiological process in which the body facilitates the repair of a bone fracture. In the process of fracture healing, several phases of recovery facilitate the proliferation and protection of the areas surrounding fractures and dislocations. The length of the process depends on the extent of the injury, and usual margins of two to three weeks are given for the reparation of most upper bodily fractures; anywhere above four weeks given for lower bodily injury. The healing process is mainly determined by the "periosteum" (the connective tissue membrane covering the bone). The periosteum is one source of precursor cells which develop into "chondroblasts" and osteoblasts that are essential to the healing of bone. The bone marrow (when present), endosteum, small blood vessels, and fibroblasts are other sources of precursor cells.

In another embodiment, compounds of Formula I or Table I, or pharmaceutically acceptable salts thereof, that are stimulators of sGC and their pharmaceutically acceptable salts thereof, are therefore useful in the treatment of the following types of diseases, disorders or conditions in which stimulation of the processes of wound or bone healing would be desirable:

wound or ulcer healing in diabetics; microvascular perfusion improvement; microvascular perfusion improvement following injury or to counteract the inflammatory response in perioperative care; anal fissures; diabetic ulcers; diabetic foot ulcers); bone healing; osteoclastic bone resorption and remodeling; and new bone formation.

The term "connective tissue" (CT) refers to a kind of animal tissue that supports, connects, or separates different types of tissues and organs of the body. It is one of the four general classes of animal tissues, the others being epithelial, muscle, and nervous tissues. Connective tissue is found everywhere, including in the central nervous system. It is located in between other tissues. All CT has three main components—ground substances, fibers and cells—and all these components are immersed in the body fluids.

The term "connective tissue disorder or condition" refers to any condition that involves abnormalities in connective tissue in one or more parts of the body. Certain disorders are characterized by over-activity of the immune system with resulting inflammation and systemic damage to the tissues, usually with replacement of normal tissue (e.g., normal tissue of a certain organ) with connective tissue. Other disorders involve biochemical abnormalities or structural defects of the connective tissue itself. Some of these disorders are inherited, and some are of unknown etiology.

When connective tissue diseases are of autoimmune origin they are classified as "rheumatic disorders", "autoimmune rheumatic disorders" or "autoimmune collagen-vascular disorders".

In an "autoimmune disorder", antibodies or other cells produced by the body attack the body's own tissues. Many autoimmune disorders affect connective tissue in a variety of organs. In autoimmune disorders, inflammation and the immune response may result in connective tissue damage, around the joints and also in other tissues, including vital organs, such as the kidneys or organs of the gastrointestinal tract. The sac that surrounds the heart (pericardium), the membrane that covers the lungs (pleura), the mediastinum (an undelineated group of structures in the thorax, surrounded by loose connective tissue, containing the heart, the great vessels of the heart, the esophagus, the trachea, the phrenic nerve, the cardiac nerve, the thoracic duct, the thymus, and the lymph nodes of the central chest) and even the brain may be affected.

The term "fibrosis" as used herein refers to the accumulation of connective tissue or fibrous tissue (scar tissue, collagen) in a certain organ or part of the body. If fibrosis arises from a single cell line it is called a "fibroma". Fibrosis occurs as the body attempts to repair and replace damaged cells, and thus can be a reactive, benign or a pathological state. Physiological fibrosis is similar to the process of scarring. A pathological state develops when the tissue in question is repeatedly and continuously damaged. A single episode of injury, even if severe, does not usually cause fibrosis. If injury is repeated or continuous (for instance as it occurs in chronic hepatitis) the body attempts to repair the damage, but the attempts result instead in excessive accumulation of scar tissue. Scar tissue starts to replace regular tissue of the organ which performs certain functions that the scar tissue is not able to perform; it can also interfere with blood flow and limit blood supply to other cells. As a result, these other functional cells start to die and more scar tissue is formed. When this occurs in the liver, blood pressure in the vein that carries blood from the intestine to the liver (portal vein) increases, giving rise to the condition known as "portal hypertension".

The term "sclerosis" refers to the hardening or stiffening of tissue or a structure or organ that would normally be flexible, usually by replacement of normal organ specific tissue with connective tissue.

There are many types of fibroses or fibrotic diseases including but not limited to pulmonary fibrosis (idiopathic pulmonary fibrosis, cystic fibrosis), fibrosis of the liver (or "cirrhosis"), endomyocardial fibrosis, old myocardial infarction, atrial fibrosis, mediastinal fibrosis, myelofibrosis (affecting the bone marrow), retroperitoneal fibrosis, progressive massive fibrosis (affects the lungs), nephrogenic fibrosis (affecting the skin), Crohn's disease, arthrofibrosis, Peyronie's disease (affecting the penis), Dupuytren's contracture (affecting the hands and fingers), some forms of adhesive capsulitis (affecting the shoulders).

There are many types of scleroses or "sclerotic diseases" including but not limited to Amyotrophic Lateral Sclerosis (ALS); atherosclerosis; focal segmental glomerulosclerosis and nephrotic syndrome; hippocampal sclerosis (affecting the brain); lichen sclerosus (a disease that hardens connective tissue of the vagina and penis); liver sclerosis (cirrhosis); multiple sclerosis or focal sclerosis (diseases that affects coordination); osteosclerosis (a disease in which bone density is significantly reduced); otosclerosis (disease affecting the ears); tuberous sclerosis (rare genetic disease affecting multiple systems); primary sclerosing cholanginitis (hardening of the bile duct); primary lateral sclerosis (progressive muscle weakness in the voluntary muscles); and keloids.

The term "scleroderma" or "systemic sclerosis" or "progressive systemic scleroderma" refers to a condition which involves scarring of the joints, skin and internal organs as well as blood vessel abnormalities. Systemic sclerosis can sometimes occur in limited forms, for examples sometimes affecting just the skin or mainly only certain parts of the skin or as CREST syndrome (wherein peripheral areas of the skin but not the trunk are involved). The usual initial symptom of systemic sclerosis is swelling, then thickening and tightening of the skin at the end of the fingers. "Raynaud's phenomenon", in which fingers suddenly and temporarily become very pale and tingle or become numb, painful or both, is common.

The term "polymyositis" refers to muscle inflammation. The term "dermatomyositis", refers to muscle inflammation that is accompanied by skin inflammation. The term "polychondritis" refers to cartilage inflammation.

The term "oesinophilic fasciitis" refers to a rare disorder in which oesinophilic immune cells are released and results in inflammation and hardening of the "fasciae" which is the layer of tough fibrous tissue beneath the skin, on top and between the muscles. The fasciae becomes painfully inflamed and swollen and gradually hardens in the arms and legs. As the skin of the arms and legs progressively hardens, they become difficult to move. Eventually they become stuck in unusual positions. Sometimes, if the arms are involved the person may develop carpal tunnel syndrome.

In another embodiment, specific diseases of disorders which may be treated and/or prevented by administering an sGC stimulator of Formula I or Table I, or pharmaceutically acceptable salts thereof, that are stimulators of sGC, and their pharmaceutically acceptable salts thereof, include but are not limited to the following type of diseases involving inflammation, autoimmunity or fibrosis (i.e., fibrotic diseases):

urogenital system and kidney disorders: diabetic nephropathy; renal fibrosis and renal failure resulting from chronic kidney diseases or insufficiency; renal fibrosis and renal failure due to accumulation/deposition and tissue injury; renal sclerosis; progressive sclerosis; glomerulonephritis; focal segmental glomerulosclerosis; nephrotic syndrome; prostate hypertrophy; kidney fibrosis; interstitial renal fibrosis;

pulmonary system disorders: pulmonary fibrosis; idiopathic pulmonary fibrosis; cystic fibrosis; progressive massive fibrosis; progressive massive fibrosis thataffects the lungs);

disorders affecting the heart: endomyocardial fibrosis; old myocardial infarction; atrial fibrosis; cardiac interstitial fibrosis; cardiac remodeling and fibrosis; cardiac hypertrophy;

disorders of the liver and related organs: liver sclerosis or cirrhosis; liver cirrhosis associated with chronic liver disease; hepatic fibrosis; hepatic stellate cell activation; NASH; hepatic fibrous collagen and total collagen accumulation; liver disease of necro-inflammatory and/or of immunological origin; primary biliary cirrhosis; primary sclerosing cholanginitis; other cholestatic liver diseases: those associated with granulomatous liver diseases, liver malignancies, intrahepatic cholestasis of pregnancy, hepatitis, sepsis, drugs or toxins, graft-versus-host disease, post-liver transplantation, choledocholithiasis, bile duct tumors, pancreatic carcinoma, Mirizzi's syndrome, AIDS cholangiopathy or parasites; schistosomiasis; hepatocellular carcinoma;

digestive diseases or disorders: Crohn's disease; Ulcerative Colitis; sclerosis of the gastro-intestinal tract; achalasia;

diseases of the skin or the eyes: nephrogenic fibrosis; keloids; fibrotic topical or skin disorders or conditions; dermal fibrosis; scleroderma, skin fibrosis; morphea; hypertrophic scars; naevi;

proliferative vitroretinopathy; sarcoids; granulomas; eye fibrosis;

diseases affecting the nervous system: Amyotrophic Lateral Sclerosis (ALS); hippocampal sclerosis, multiple sclerosis (MS); focal sclerosis; primary lateral sclerosis;

diseases of the bones; osteosclerosis;

otosclerosis; other hearing diseases or disorders; hearing impairment, partial or total hearing loss; partial or total deafness; tinnitus; noise-induced hearing loss;

other diseases involving autoimmunity, inflammation or fibrosis: scleroderma; localized scleroderma or circumscribed scleroderma; mediastinal fibrosis; fibrosis mediastinitis; myelofibrosis; retroperitoneal fibrosis; arthrofibrosis; Peyronie's disease; Dupuytren's contracture; lichen sclerosus; some forms of adhesive capsulitis; atherosclerosis; tuberous sclerosis; systemic sclerosis; polymyositis; dermatomyositis; polychondritis; oesinophilic fasciitis; Systemic Lupus Erythematosus or lupus; bone marrow fibrosis, myelofibrosis or osteomyelofibrosis; sarcoidosis; uterine fibroids; endometriosis.

In another embodiment, specific diseases of disorders which may be treated and/or prevented by administering an sGC stimulator of Formula I or Table I, or pharmaceutically acceptable salts thereof, that are stimulators of sGC, and their pharmaceutically acceptable salts thereof, include but are not limited to: certain types of cancers; Sickle Cell Disease; Sickle Cell Anemia; cancer metastasis; osteoporosis; gastroparesis; functional dyspepsia; diabetic complications; alopecia or hair loss; diseases associated with endothelial dysfunction; neurologic disorders associated with decreased nitric oxide production; arginosuccinic aciduria; neuromuscular diseases: Duchenne muscular dystrophy (DMD), Becker muscular dystrophy (BMD), limb girdle muscular dystrophies, distal myopathies, type I and type II myotonic dystrophies, facio-scapulo-peroneal muscular dystrophy, autosomal and X-linked Emery-Dreifuss muscular dystrophy, oculopharyngeal muscular dystrophy, amyotrophic lateral sclerosis and spinal muscle atrophy (SMA) In some embodiments, the invention relates to a method of treating a disease, health condition or disorder in a subject, comprising administering a therapeutically effective amount of a compound of Formula I or Table I, or pharmaceutically acceptable salts thereof, or a pharmaceutically acceptable salt thereof, to the subject in need of treatment, wherein the disease, health condition or disorder is selected from one of the diseases listed above.

In another embodiment, compounds of the invention can be delivered in the form of implanted devices, such as stents. A stent is a mesh 'tube' inserted into a natural passage/conduit in the body to prevent or counteract a disease-induced, localized flow constriction. The term may also refer to a tube used to temporarily hold such a natural conduit open to allow access for surgery.

A drug-eluting stent (DES) is a peripheral or coronary stent (a scaffold) placed into narrowed, diseased peripheral or coronary arteries that slowly releases a drug to block cell proliferation, usually smooth muscle cell proliferation. This prevents fibrosis that, together with clots (thrombus), could otherwise block the stented artery, a process called restenosis. The stent is usually placed within the peripheral or coronary artery by an Interventional Cardiologist or Interventional Radiologist during an angioplasty procedure. Drugs commonly used in DES in order to block cell proliferation include paclitaxel or rapamycin analogues.

In some embodiments of the invention, a sGC stimulator of the invention can be delivered by means of a drug-eluting stent coated with said sGC stimulator. A drug-eluting stent coated with a sGC stimulator of the invention may be useful in the prevention of stent restenosis and thrombosis during percutaneous coronary interventions. A drug-eluting stent coated with a sGC stimulator of the invention may be able to prevent smooth cell proliferation as well as to assist re-vascularization and re-generation of the endothelial tissue of the artery in which the stent is inserted.

An alternative to percutaneous coronary intervention for the treatment of intractable angina due to coronary artery occlusive disease is the procedure named Coronary Artery Bypass Grafting (CABG). CABG provides only palliation of an ongoing process that is further complicated by the rapid development of graft atherosclerosis. The saphenous vein graft is the most commonly used conduit in CABG surgery. The long-term clinical success of venous CABG is hampered for three main reasons: accelerated graft atherosclerosis, incomplete endothelialization and thrombosis.

In some embodiments, a sGC stimulator of the invention can be used for the prevention of saphenous graft failure during CABG. Compounds of the invention may assist the process of endothelialization and help prevent thrombosis. In this indication, the sGC stimulator is delivered locally in the form of a gel.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Formula I or Table I, or a pharmaceutically acceptable salt thereof, to the subject in need of the treatment. Alternatively, the invention provides the use of a compound of Formula I or Table I, or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Formula I or Table I, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernible symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments the terms "treat", "treatment" and "treating" refer to the inhibition of the progression of an sGC, cGMP and/or NO mediated condition, either physically by, e.g., stabilization of a discernible symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g., a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I or Table I or a pharmaceutically acceptable salt thereof and a second amount of an additional suitable therapeutic agent.

In one embodiment of this invention, a compound of Formula I or Table I, or a pharmaceutically acceptable salt thereof, and the additional therapeutic agent are each administered in an effective amount (i.e., each in an amount which would be therapeutically effective if administered alone). In another embodiment, the compound of Formula I or Table I, or a pharmaceutically acceptable salt thereof, and the additional therapeutic agent are each administered in an amount which alone does not provide a therapeutic effect (a sub-therapeutic dose). In yet another embodiment, the compound of Formula I or Table I, or a pharmaceutically acceptable salt thereof, can be administered in an effective amount, while the additional therapeutic agent is administered in a sub-therapeutic dose. In still another embodiment, the compound of Formula I or Table I, or a pharmaceutically acceptable salt thereof, can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Formula I or Table I, or a pharmaceutically acceptable salt thereof, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I or Table I, or a pharmaceutically acceptable salt thereof, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of Formula I or Table I, or a pharmaceutically acceptable salt thereof, either administered separately or in the same pharmaceutical composition include, but are not limited to:

(1) Endothelium-derived releasing factor (EDRF);

(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitroglycerin), the nitrate ester of glycerol; sodium-nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CI-NOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), Sodium Nitroprusside, V-Pyrro-NO, S-nitrosoglutathione mono-ethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650,442, 5,700,830, 5,632,981, 6,290,981, 5,691,423 5,721,365, 5,714,511, 6,511,911, and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin IX, arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxylagmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g., 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schlfer et al., Journal of Thrombosis and Homeostasis 2005; Volume 3, Supplement 1: abstract number P1487);

(6) NO independent heme-independent sGC activators, including, but not limited to: BAY 58-2667 (see patent publication DE19943635)

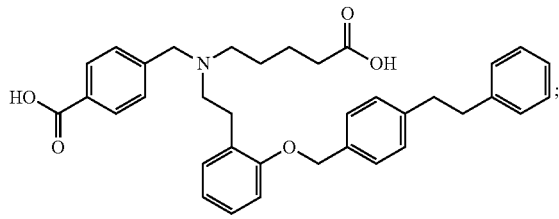 [SMILES: O=C(O)CCCCN(CCc1ccccc1OCc1ccc(CCc2ccccc2)cc1)Cc1ccc(C(=O)O)cc1]

HMR-1766 (ataciguat sodium, see patent publication WO2000002851)

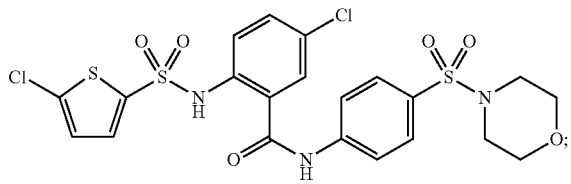 [SMILES: O=C(Nc1ccc(S(=O)(=O)N2CCOCC2)cc1)c1cc(Cl)ccc1NS(=O)(=O)c1ccc(Cl)s1]

S3448
(2-(4-chloro-phenylsulfonylamino)-4,5-dimethoxy-N-(4-(thiomorpholine-4-sulfonyl)-phenyl)-benzami de (see patent publications DE19830430 and WO2000002851)

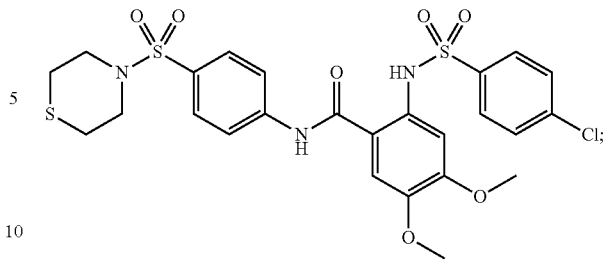

and
HMR-1069 (Sanofi-Aventis).

(7) Heme-dependent sGC stimulators including, but not limited to:
YC-1 (see patent publications EP667345 and DE19744026)

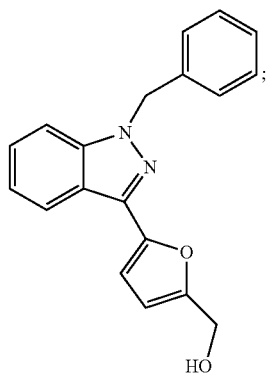 [SMILES: OCc1ccc(-c2nn(Cc3ccccc3)c3ccccc23)o1]

Riociguat (BAY 63-2521, Adempas, commercial product, described in DE19834044)

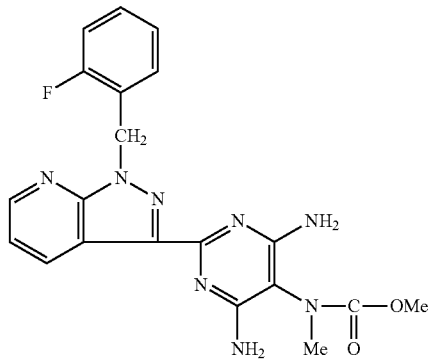 [SMILES: COC(=O)N(C)c1c(N)nc(-c2nn(Cc3ccccc3F)c3ncccc23)nc1N]

Neliciguat (BAY 60-4552, described in WO 2003095451)

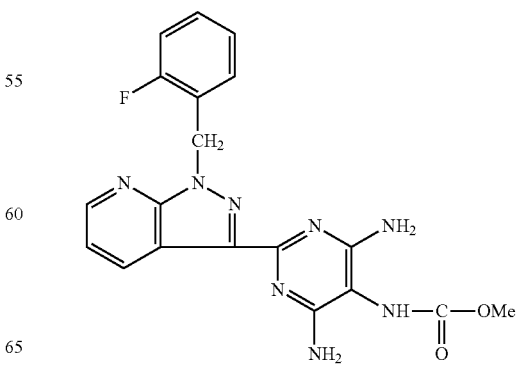

Vericiguat (BAY 1021189, clinical backup to Riociguat),

BAY 41-2272 (described in DE19834047 and DE19942809)

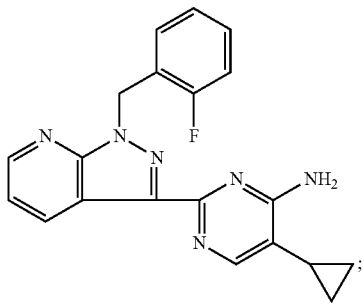 [SMILES: Nc1nc(-c2nn(Cc3ccccc3F)c3ncccc23)ncc1C1CC1]

BAY 41-8543 (described in DE19834044)

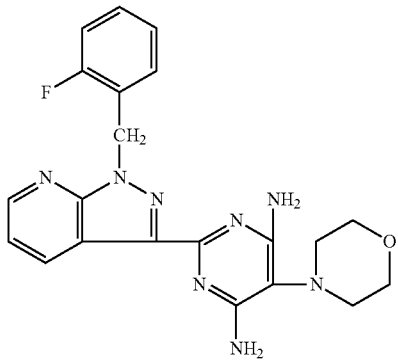 [SMILES: Nc1nc(-c2nn(Cc3ccccc3F)c3ncccc23)nc(N)c1N1CCOCC1]

Etriciguat (described in WO 2003086407)

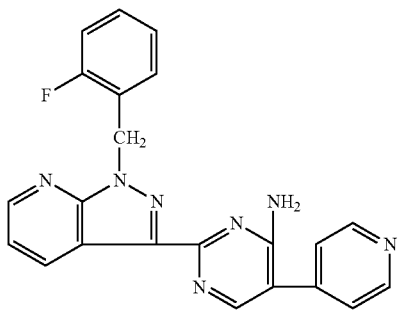 [SMILES: Nc1nc(-c2nn(Cc3ccccc3F)c3ncccc23)ncc1-c1ccncc1]

CFM-1571 (see patent publication WO2000027394)

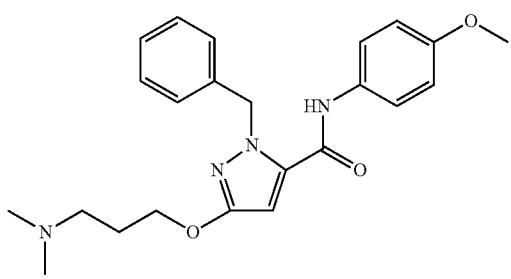

A-344905, its acrylamide analogue A-350619 and the aminopyrimidine analogue A-778935.

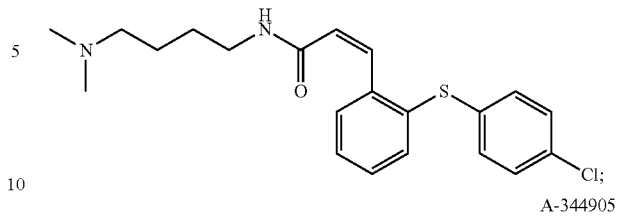

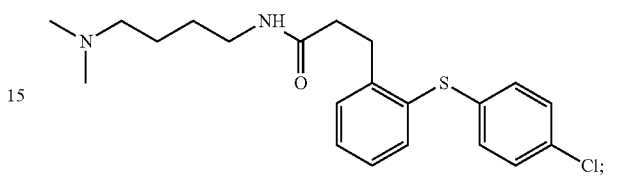

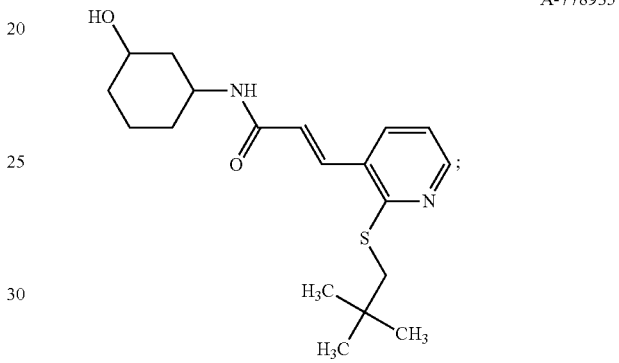

Compounds disclosed in one of publications: US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds disclosed in Tetrahedron Letters (2003), 44(48): 8661-8663.

(8) Compounds that inhibit the degradation of cGMP, such as:

PDE5 inhibitors, such as, for example, Sildenafil (Viagra®) and other related agents such as Avanafil, Lodenafil, Mirodenafil, Sildenafil citrate (Revatio®), Tadalafil (Cialis® or Adcirca®), Vardenafil (Levitra®) and Udenafil; Alprostadil; and Dipyridamole; PF-00489791

PDE9 inhibitors, such as, for example, PF-04447943;

(9) Calcium channel blockers such as:

Dihydropyridine calcium channel blockers: Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Diltiazem, Efonidipine (Landel), Felodipine (Pendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Isradipine (Lomir);

Phenylalkylamine calcium channel blockers: Verapamil (Calan, Isoptin)

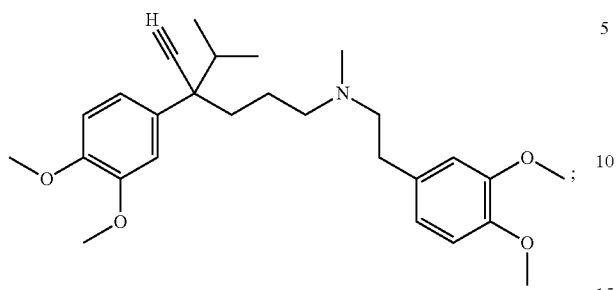

Gallopamil (Procorum, D600);
Benzothiazepines: Diltiazem (Cardizem);

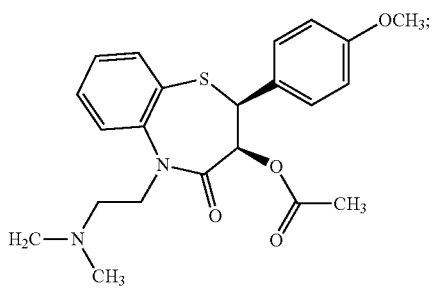 [SMILES: COc1ccc([C@@H]2Sc3ccccc3N(CCN(C)C)C(=O)[C@@H]2OC(C)=O)cc1]

Nonselective calcium channel inhibitors such as: mibefradil, bepridil and fluspirilene, fendiline;
(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S; dual/nonselective endothelin antagonist Actelion-1, that entered clinical trials in 2008;
(11) Prostacyclin derivatives or analogues: for instance prostacyclin (prostaglandin $I_2$), Epoprostenol (synthetic prostacyclin, marketed as Flolan®); Treprostinil (Remodulin®), Iloprost (Ilomedin®), Iloprost (marketed as Ventavis®); oral and inhaled forms of Remodulin® that are under development; Beraprost, an oral prostanoid available in Japan and South Korea;
(12) Antihyperlipidemics such as: bile acid sequestrants (e.g., Cholestyramine, Colestipol, Colestilan and Colesevelam); statins such as Atorvastatin, Simvastatin, Lovastatin, Fluvastatin, Pitavastatin, Rosuvastatin and Pravastatin; cholesterol absorption inhibitors such as Ezetimibe; other lipid lowering agents such as Icosapent ethyl ester, Omega-3-acid ethyl esters, Reducol; fibric acid derivatives such as Clofibrate, Bezafibrate, Clinofibrate, Gemfibrozil, Ronifibrate, Binifibrate, Fenofirate, Ciprofibrate, Choline fenofibrate; nicotinic acid derivatives such as Acipimox and Niacin; also combinations of statins, niacin, intestinal cholesterol absorption-inhibiting supplements (ezetimibe and others) and fibrates; antiplatelet therapies such as Clopidogrel bisulfate;
(13) Anticoagulants, such as the following types:
  Coumarines (Vitamin K antagonists): Warfarin® (Coumadin) mostly used in the US and UK; Acenocoumarol® and Phenprocoumon®, mainly used in other countries; Phenindione®;
  Heparin and derivative substances such as: Heparin; low molecular weight heparin, Fondaparinux and Idraparinux;
  Direct thrombin inhibitors such as: Argatroban, Lepirudin, Bivalirudin and Dabigatran; Ximelagatran (Exanta®), not approved in the US;
  Tissue plasminogen activators, used to dissolve clots and unblock arteries, such as Alteplase;
(14) Antiplatelet drugs: for instance thienopyridines such as Lopidogrel and Ticlopidine; Dipyridamole; Aspirin;
(15) ACE inhibitors, for example the following types:
  Sulfhydryl-containing agents such as Captopril (trade name Capoten®), the first ACE inhibitor and Zofenopril;
  Dicarboxylate-containing agents such as Enalapril (Vasotec/Renitec®); Ramipril (Altaceffritace/Ramace/Ramiwin®); Quinapril (Accupril®), Perindopril (Coversyl/Aceon®); Lisinopril (Lisodur/Lopril/Novatec/Prinivil/Zestril®) and Benazepril (Lotensin®);
  Phosphonate-containing agents such as: Fosinopril;
  Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;
  Other ACE inhibitors such as Alacepril, Delapril, Cilazapril, Imidapril, Trandolapril, Temocapril, Moexipril, Spirapril,
(16) Supplemental oxygen therapy;
(17) Beta blockers, such as the following types:
  Non-selective agents: Alprenolol, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Oxprenonol, Acebutolol, Sotalol, Mepindolol, Celiprolol, Arotinolol, Tertatolol, Amosulalol, Nipradilol, Propranolol® and Timolol®;
  $β_1$-Selective agents: Acebutolol® (has intrinsic sympathomimetic activity), Atenolol®, Betaxolol®, Bisoprolol®, Celiprolol®, Dobutamine hydrochloride, Irsogladine maleate, Carvedilol, Talinolol, Esmolol®, Metoprolol® and Nebivolol®;
  $β_2$-Selective agents: Butaxamine® (weak α-adrenergic agonist activity);
(18) Antiarrhythmic agents such as the following types:
  Type I (sodium channel blockers): Quinidine, Lidocaine, Phenytoin, Propafenone
  Type III (potassium channel blockers): Amiodarone, Dofetilide, Sotalol
  Type V: Adenosine, Digoxin
(19) Diuretics such as: Thiazide diuretics, e.g., Chlorothiazide, Chlorthalidone, and Hydrochlorothiazide, Bendroflumethiazide, Cyclopenthiazide, Methyclothiazide, Polythiazide, Quinethazone, Xipamide, Metolazone, Indapamide, Cicletanine; Loop diuretics, such as Furosemide and Toresamide; potassium-sparing diuretics such as Amiloride, Spironolactone, Canrenoate potassium, Eplerenone and Triamterene; combinations of these agents; other diuretics such as Acetazolamid and Carperitide
(20a) Direct-acting vasodilators such as Hydralazine hydrochloride, Diazoxide, Sodium nitroprusside, Cadralazine; other vasodilators such as Isosorbide dinitrate and Isosorbide 5-mononitrate;
(20b) Exogenous vasodilators such as:
  Adenocard®, an adenosine agonist, primarily used as an anti-arrhythmic;

Alpha blockers (which block the vasoconstricting effect of adrenaline):

Alpha-1-adrenoceptor antagonists such as Prazosin, Indoramin, Urapidil, Bunazosin, Terazosin, Doxazosin Atrial natriuretic peptide (ANP);

Ethanol;

Histamine-inducers, which complement proteins C3a, C4a and C5a work by triggering histamine release from mast cells and basophil granulocytes;

Tetrahydrocannabinol (THC), major active chemical in marijuana which has minor vasodilatory effects;

Papaverine, an alkaloid found in the opium poppy *Papaver somniferum;*

(21) Bronchodilators: there are two major types of bronchodilator, f agonists and anticholinergics, exemplified below:

$\beta_2$ agonists: Salbutamol® or albuterol (common brand name: Ventolin) and Terbutaline® are short acting $\beta_2$ agonists for rapid relief of COPD symptoms. Long acting $\beta_2$ agonists (LABAs) such as Salmeterol® and Formoterol®;

anticholinergics: Ipratropium® is the most widely prescribed short acting anticholinergic drug. Tiotropium® is the most commonly prescribed long-acting anticholinergic drug in COPD;

Theophylline®, a bronchodilator and phosphodiesterase inhibitor;

(22) Corticosteroids: such as beclomethasone, methylprednisolone, betamethasone, prednisone, prednisolone, triamcinolone, dexamethasone, fluticasone, flunisolide and hydrocortisone, and corticosteroid analogs such as budesonide

(23) Dietary supplements such as, for example: omega-3 oils; folic acid, niacin, zinc, copper, Korean red *ginseng* root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Testosterone transdermal patch; Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;

(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);

(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(28) Cyclooxygenase-2 (COX-2) inhibitors such as celecoxib (Celebrex®), rofecoxib (Vioxx®), valdecoxib, etoricoxib, parecoxib and lumiracoxib;

(opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and

(29) Anti-diabetic agents such as insulin and insulin mimetics, sulfonylureas (e.g., Glyburide, Glybenclamide, Glipizide, Gliclazide, Gliquidone, Glimepiride, Meglinatide, Tolbutamide, Chlorpropamide, Acetohexamide, Tolazamide), biguanides, e.g., metformin (Glucophage®), α-glucosidase inhibitors (such as Acarbose, Eparestat, Voglibose, Miglitol), thiazolidinone compounds, e.g., rosiglitazone (Avandia®), troglitazone (Rezulin®), ciglitazone, pioglitazone (Actos®) and englitazone; insulin sensitizers such as Pioglitazone and Rosiglitazone; Insulin secretagogues such as Repaglinide, Nateglinide and Mitiglinide; Incretin mimetics such as Exanatide and Liraglutide; Amylin analogues such as Pramlintide; glucose lowering agents such as Chromium picolinate (optionally combined with biotin); dipeptidyl peptidase IV inhibitors such as Sitagliptin, Vildagliptin, Saxagliptin, Alogliptin and Linagliptin; vaccines currently being developed for the treatment of diabetes; AVE-0277, Alum-GAD, BHT-3021, IBC-VSO1; cytokine targeted therapies in development for the treatment of diabetes such as Anakinra, Canakinumab, Diacerein, Gevokizumab, LY-2189102, MABP-1, GIT-027;

(30) HDL cholesterol-increasing agents such as Anacetrapib, MK-524A, CER-001, DRL-17822, Dalcetrapib, T-302, RVX-000222, TA-8995;

(31) Antiobesity drugs such as Methamphetamine hydrochloride, Amfepramone hydrochloride (Tenuate®), Phentermine (Ionamin®), Benzfetamine hydrochloride (Didrex®), Phendimetrazine tartrate (Bontril®, Prelu-2 ®, Plegine®), Mazindol (Sanorex®), Orlistat (Xenical®), Sibutramine hydrochloride monohydrate (Meridia®, Reductil®), Rimonabant (Acomplia®), Amfepramone, Chromium picolinate, RM-493, TZP-301; combination such as Phentermine/Topiramate, Bupropion/Naltrexone, Sibutramine/Metformin, Bupropion SR/Zonisamide SR, Salmeterol, xinafoate/fluticasone propionate; Lorcaserin hydrochloride, Phentermine/topiramate, Bupropion/naltrexone, Cetilistat, Exenatide, KI-0803, Liraglutide, Metformin hydrochloride, Sibutramine/Metformin, 876167, ALS-L-1023, Bupropion SR/Zonisamide SR, CORT-108297, Canagliflozin, Chromium picolinate, GSK-1521498, LY-377604, Metreleptin, Obinepitide, P-57AS3, PSN-821, Salmeterol xinafoate/fluticasone propionate, Sodium tungstate, Somatropin (recombinant), TM-30339, TTP-435, Tesamorelin, Tesofensine, Velneperit, Zonisamide, BMS-830216, ALB-127158, AP-1030, ATHX-105, AZD-2820, AZD-8329, Beloranib hemioxalate, CP-404, HPP-404, ISIS-FGFR4Rx, Insulinotropin, KD-3010PF, 05212389, PP-1420, PSN-842, Peptide YY3-36, Resveratrol, S-234462; S-234462, Sobetirome, TM-38837, Tetrahydrocannabivarin, ZYO-1, beta-Lapachone;

(32) Angiotensin receptor blockers such as Losartan, Valsartan, Candesartan cilexetil, Eprosaran, Irbesartan, Telmisartan, Olmesartran medoxomil, Azilsartan medoxomil;

(33) Renin inhibitors such as Aliskiren hemifumirate;

(34) Centrally acting alpha-2-adrenoceptor agonists such as Methyldopa, Clonidine, Guanfacine;

(35) Adrenergic neuron blockers such as Guanethidine, Guanadrel;

(36) Imidazoline I-1 receptor agonists such as Rimenidine dihydrogen phosphate and Moxonidine hydrochloride hydrate;

(37) Aldosterone antagonists such as Spironolactone and Eplerenone

(38) Potassium channel activators such as Pinacidil

(39) Dopamine D1 agonists such as Fenoldopam mesilate; Other dopamine agonists such as Ibopamine, Dopexamine and Docarpamine;

(40) 5-HT2 antagonists such as Ketanserin;

(42) Vasopressin antagonists such as Tolvaptan;

(43) Calcium channel sensitizers such as Levosimendan or activators such as Nicorandil;

(44) PDE-3 inhibitors such as Amrinone, Milrinone, Enoximone, Vesnarinone, Pimobendan, Olprinone;

(45) Adenylate cyclase activators such as Colforsin dapropate hydrochloride;

(46) Positive inotropic agents such as Digoxin and Metildigoxin; metabolic cardiotonic agents such as Ubidecarenone; brain naturetic peptides such as Nesiritide;

(49) Drugs used for the treatment of erectile dysfunction such as Alprostadil, Aviptadil, Phentolamine mesilate, Weige, Alprostadil;

(53) Antiobesity drugs:

| Drugs marketed for the treatment of obesity | | | |
|---|---|---|---|
| Methamphetamine hydrochloride (Desoxyn) | Abbott | Noradrenergic, alpha- and beta-adrenoceptor agonist | 1943 (U.S.) |
| Amfepramone hydrochloride (Tenuate) | Sanofi | Noradrenergic release stimulant | 1959 (U.S.) |
| Phentermine (Ionamin) | UCB Celltech | Noradrenergic release stimulant | 1959 (U.S.) |
| Benzfetamine hydrochloride (Didrex) | Pfizer | Noradrenergic release stimulant | 1960 (U.S.) |
| Phendimetrazine tartrate (Bontril, Prelu-2, Plegine) | Pfizer | Noradrenergic release stimulant | 1961 (U.S.) |
| Mazindol (Sanorex) | Novartis | Noradrenergic reuptake inhibitor | 1973 (U.S.) |
| Orlistat (Xenical) | Roche | Pancreatic lipase inhibitor | 1998 (New Zealand) |

(54) Drugs used for the treatment of Alzheimer's disease: e.g., cholinesterase inhibitors prescribed for mild to moderate Alzheimer's disease, including Razadyne® (galantamine), Exelon® (rivastigmine), and Aricept® (donepezil), Cognex® (tacrine); Namenda® (memantine), an N-methyl D-aspartate (NMDA) antagonist, and Aricept®, prescribed to treat moderate to severe Azheimer's disease; vitamin E (an anti-oxidant).

(55) Antidepressants: tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®); SNRIs (e.g., venlafaxine and reboxetine); dopaminergic antidepressants (e.g., bupropion and aminestine).

(56) Neuroprotective agents: e.g., memantine, L-dopa, bromocriptine, pergolide, talipexol, pramipexol, cabergoline, neuroprotective agents currently under investigation including anti-apoptotic drugs (CEP 1347 and CTCT346), lazaroids, bioenergetics, antiglutamatergic agents and dopamine receptors. Other clinically evaluated neuroprotective agents are, e.g., the monoamine oxidase B inhibitors selegiline and rasagiline, dopamine agonists, and the complex I mitochondrial fortifier coenzyme Q10.

(57) Antipsychotic medications: e.g., ziprasidone (Geodon™), risperidone (Risperdal™), and olanzapine (Zyprexa™).

(58) NEP inhibitors such as Sacubitril, Omapatrilat.

(59) Methylene Blue (MB).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g., preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

Example 1: Compound Synthesis

Compound I-1

The title compound was synthesized in 2 steps:

Step 1: Synthesis of Intermediate 4 and Intermediate 5

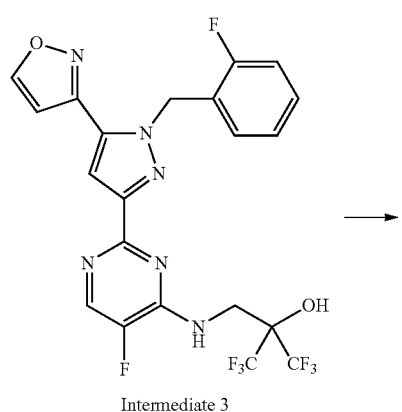

Intermediate 3

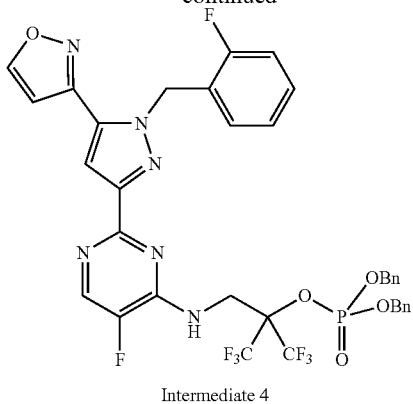

Intermediate 4

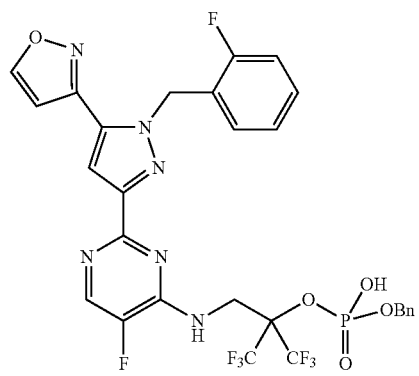

Intermediate 5

To a solution of Intermediate 3 (0.3 g, 1 equiv.; this compound was synthesized previously as described in WO2014144100) and dibenzyl diisopropylphosphoramidite (0.38 g, 2 equiv.) in dichloromethane (6 ml) was added to 1H-tetrazole as a 0.45 M solution in acetonitrile (4.37 ml, 3.5 equiv.) and the reaction mixture was stirred at room temperature for 30 minutes. The reaction mixture was then cooled to 0° C., meta-chloroperoxybenzoic acid (m-CPBA, 0.29 g, 3 equiv.) was added, and the reaction was allowed to warm up to room temperature with stirring overnight. The reaction was concentrated in vacuo, diluted with methanol (1 ml), and the crude material was purified via reverse phase HPLC utilizing a 5-75% acetonitrile:water with 0.1% formic acid gradient to deliver dibenzyl Intermediate 4 [LCMS: Retention time=2.02 min., m/z 795.2 (M+H)] (3 mg, 0.6% yield) and benzyl Intermediate 5 [LCMS: Retention time=1.31 min., m/z 705.2 (M+H)] (5 mg, 1.2% yield) as white solids.

Step 2: Synthesis of Compound I-1

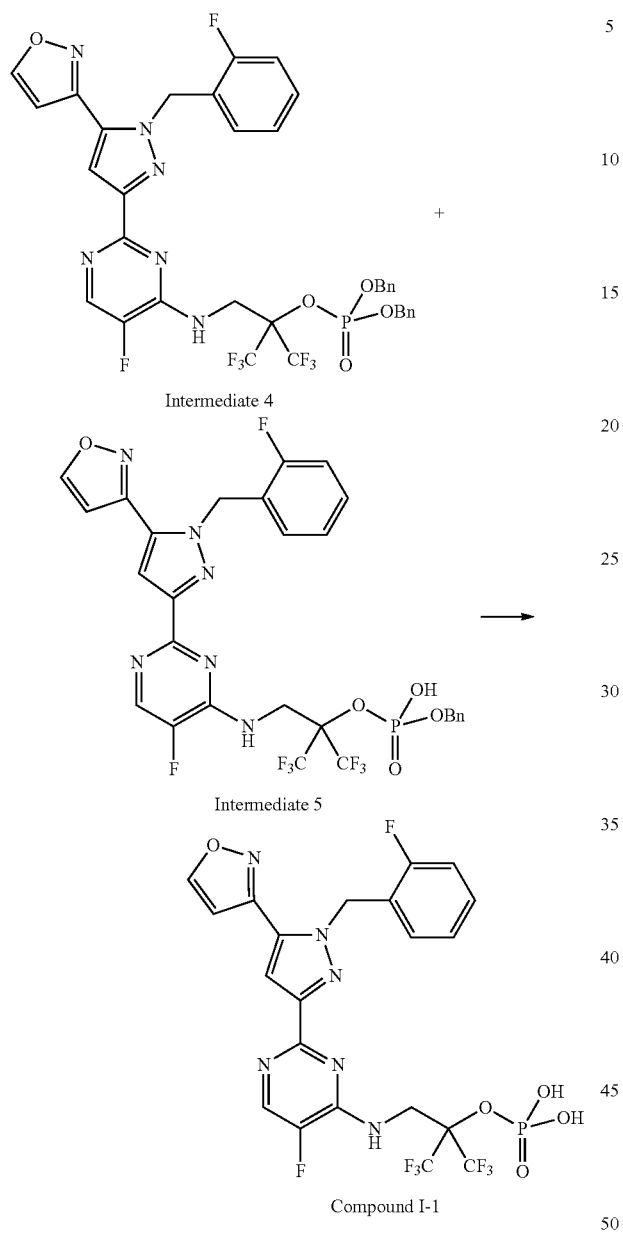

Intermediate 4

Intermediate 5

Compound I-1

To a mixture of Intermediate 4 and Intermediate 5 in methanol (3 ml) was added 5% palladium on carbon (10 equiv.). The vial was flushed with nitrogen and the reaction was stirred under a balloon of hydrogen at room temperature for 3 h. The reaction was then filtered and the solvent removed in vacuo to give Compound I-1 (6.1 mg, 79% yield) as a white solid.

$^1$H NMR (500 MHz, CD$_3$OD) ppm 8.81 (s, 1H), 8.34 (d, 1H), 7.56 (s, 1H), 7.29 (d, 1H), 7.08 (m, 2H), 6.97 (m, 1H), 6.94 (t, 1H), 6.02 (s, 2H), 4.87 (s, 2H). LCMS: retention time=1.11 min, MS (ESI pos): m/z=614.8 (M+H), MS (ESI neg): m/z=612.8 (M−H)

LC-MS Method:

UPLC ESMS were obtained using a Waters Acuity UPLC system equipped with a Waters BEH C18 column (1.7 um, 2.1×50 mm), a Waters TUV detector (220 nm) and a Waters SQ mass spectrometer with electrospray ionization. Spectra were scanned in positive and negative ion mode from 200-1000 amu over 0.1 seconds. Gradient elution was used with Buffer A as water with 0.1% formic acid, and Buffer B as acetonitrile with 0.1% formic acid at 0.6 ml/min. Samples were eluted from 10% to 100% B over 2 minutes and held at 100% B for 1 min., then the column brought back to initial conditions. Total run time was 3.0 min.

Compound I-1, Alternative Synthesis Method

The compound was synthesized in two steps.

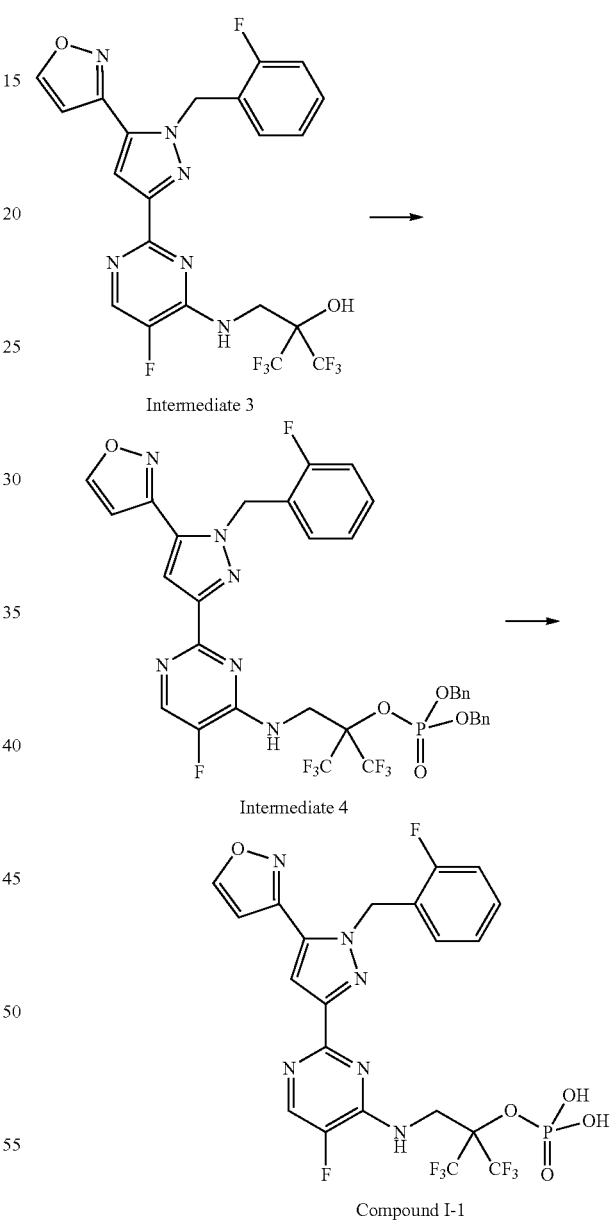

Intermediate 3

Intermediate 4

Compound I-1

Step 1: Synthesis of Intermediate 4

A solution of Intermediate 3 (0.50 g, 0.94 mmol, previously synthesized as described in WO2014144100) in tetrahydrofuran (10 mL) was cooled in ice. Lithium bis(trimethylsilyl)amide (1 M in THF, 1.2 mL, 1.2 mmol) was dripped in over 5 min and the resulting bright yellow solution was stirred for 20 min at 0° C. Tetrabenzyl diphosphate (0.70 g, 1.31 mmol) was dissolved in THF (8 mL) and cooled in ice. The pre-made Intermediate 3 lithium alkoxide solution was dripped into the diphosphate solution over 15 min and the mixture allowed to warm to room temperature over 3 hours as the ice melted. The reaction mixture was diluted with ethyl acetate (100 mL) and washed with 4×10 mL aqueous NaH₂PO₄/Na₃PO₄ buffer at pH 8, brine and dried over Na₂SO₄. The drying agent was filtered off to give a solution of crude Intermediate 4 (LCMS: m/e 795 (M+H)).

Step 2: Synthesis of Compound I-1

The solution of Intermediate 4 prepared above was transferred to a 250 mL round bottomed flask, 10% Pd/C (nominal 50% H₂O, 0.20 g) was added and the solution and vessel were purged with N₂, then H₂. The flask was sealed with a rubber septum and the mixture was stirred for 5 hours at room temperature under a hydrogen atmosphere supplied by a hydrogen-filled balloon. The mixture was filtered through Celite, the filter cake was washed with 4:1 ethyl acetate/methanol (40 mL) and the combined filtrates were concentrated by rotary evaporation. The residue was mixed with ethyl acetate (40 mL) and water (30 mL) and concentrated NH₄OH(aq) was added until the pH remained at 9 after mixing. The layers were separated and the aqueous phase was washed with 2×30 mL ethyl acetate. The aqueous phase was filtered, diluted with acetonitrile (50 mL) and lyophilized overnight to furnish Compound I-1 as an off-white powder (0.35 g, 61% yield). LCMS: m/e 615 (M+H). ¹H-NMR (500 MHz, D₂O) δ 8.70 (s, 1H), 8.10 (d, 1H), 7.30-7.35 (m, 1H), 7.31 (s, 1H), 7.13 (t, 1H), 7.08 (t, 1H), 6.95 (t, 1H), 6.83 (s, 1H), 5.78 (s, 2H), 4.67 (s, 2H) ppm.

Compound I-3

This compound was synthesized in three steps.

Step 1: Synthesis of Intermediate 2

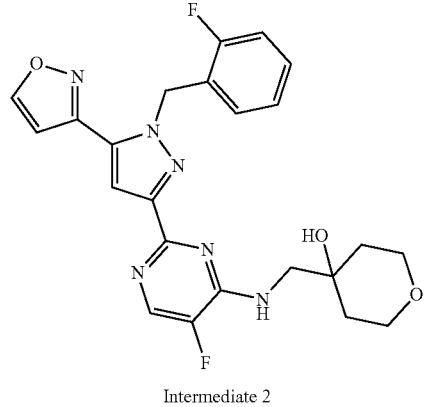

Intermediate 2

A suspension of Intermediate 1 (328 mg, 0.877 mmol, previously synthesized as described in WO2014144100), 4-(aminomethyl)tetrahydro-2H-pyran-4-ol hydrochloride (162 mg, 0.965 mmol), and triethylamine (0.611 mL, 4.38 mmol) in dioxane (3 mL) and water (1.5 mL) was heated at 90° C. for 3 hours, resulting in a light yellow homogeneous solution. The reaction mixture was allowed to cool to room temperature, diluted in water (10 mL), then 1N hydrochloric acid solution (2 mL), extracted with ethyl acetate (3×30 mL), dried over sodium sulfate, filtered and concentrated to afford the desired Intermediate 2 (373 mg, 91% yield), as a white solid. ¹H NMR (500 MHz, CD₃OD): δ (ppm): 8.76 (d, 1H), 8.09 (d, 1H), 7.42 (s, 1H), 7.25-7.29 (m, 1H), 7.07-7.11 (m, 1H), 7.02-7.06 (m, 1H), 6.89 (d, 1H), 6.83-6.87 (m, 1H), 5.96 (s, 2H), 3.74-3.80 (m, 4H), 3.71 (s, 2H), 1.74-1.80 (m, 2H), 1.57-1.61 (m, 2H). LCMS [ES]⁻: calculated for C₂₃H₂₂F₂N₆O₃, 468.17. Found: 1.07 min, 467.3.

Step 2: Synthesis of Intermediate 9

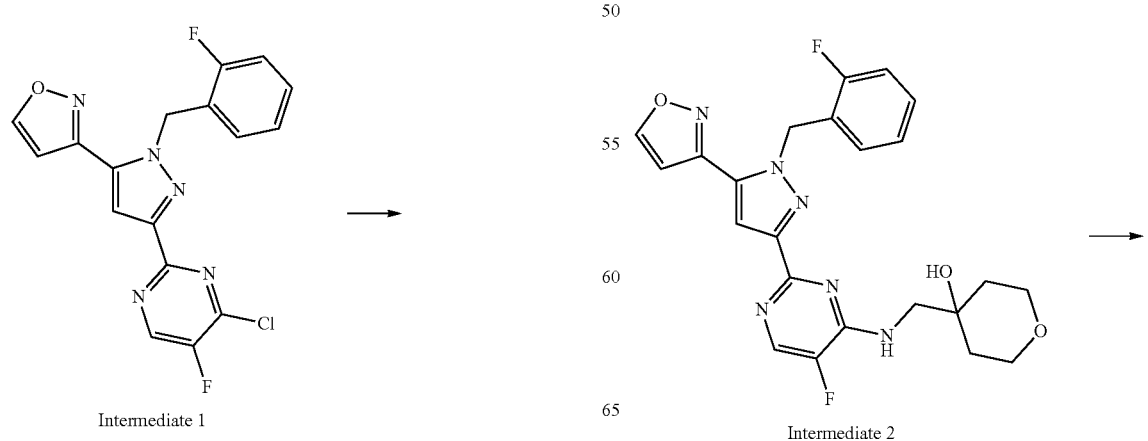

Intermediate 1   Intermediate 2

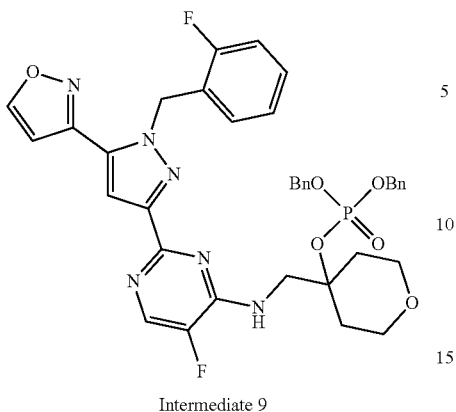

Intermediate 9

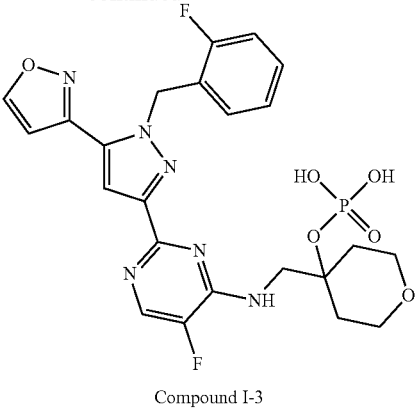

Compound I-3

To a solution of Intermediate 2 (275 mg, 0.587 mmol), in dichloromethane (8 mL) was added a 0.45 M acetonitrile solution of 1,2,3,4-tetrazole (3.91 mL, 1.76 mmol) followed by dibenzyl diisopropylphosphoramidite (0.429 mL, 1.17 mmol). The reaction mixture was stirred for 2.5 hours at room temperature, after which it was cooled to 0° C. A solution of 3-chloroperoxybenzoic acid (203 mg, 0.704 mmol) in dichloromethane (4 mL) was added, and the resulting mixture was allowed to warm up to room temperature over 1.5 hours. The reaction mixture was then concentrated to a residue and purified by silica gel chromatography utilizing a gradient of 1 to 8% methanol in dichloromethane over 60 minutes to afford a mixture of two compounds (288 mg crude mass), of which dibenzyl (4-(((5-fluoro-2-(1-(2-fluorobenzyl)-5-(isoxazol-3-yl)-1H-pyrazol-3-yl)pyrimidin-4-yl)amino)methyl)tetrahydro-2H-pyran-4-yl) phosphate (Intermediate 9) was the major component. This material was used without further purification in the next step.

Step 3: Synthesis of Compound I-3

To a suspension of the dibenzyl Intermediate 9 (280 mg) in ethyl acetate (10 mL) and absolute ethanol (10 mL) was added 10% Palladium on carbon (61.3 mg, 0.0580 mmol). The suspension was evacuated and backfilled with nitrogen three times after which a balloon charged with hydrogen gas was fitted to the reaction vial. The reaction mixture was stirred at room temperature for 12 hours, after which the reaction was filtered and concentrated to a residue. Purification was achieved by reverse phase HPLC utilizing a gradient of 5 to 95% acetonitrile in water (spiked with 0.1% trifluoroacetic acid) over 20 minutes to afford Compound I-3 (103 mg, 49% yield) as a sticky white solid.

$^1$H NMR (500 MHz, CD$_3$OD) δ (ppm): 8.81 (d, 1H), 8.23 (m, 1H), 7.65 (m, 1H), 7.28-7.33 (m, 1H), 7.09-7.13 (m, 1H), 7.05-7.08 (m, 1H), 6.99 (d, 1H), 6.94-6.97 (m, 1H), 6.02 (s, 2H), 4.22 (s, 2H), 3.84-3.89 (m, 2H), 3.74-3.82 (m, 2H), 2.04-2.08 (m, 2H), 1.84-1.89 (m, 2H). LCMS [ES]$^+$: calculated for C$_{23}$HF$_2$N$_6$O$_6$P, 548.14. Found: 0.97 min, 549.2.

Compound I-4

The title compound was synthesized in 2 steps.

Step 1: Synthesis of Intermediate 7

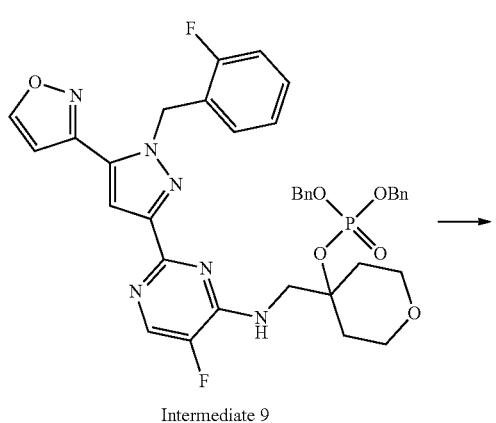

Intermediate 9

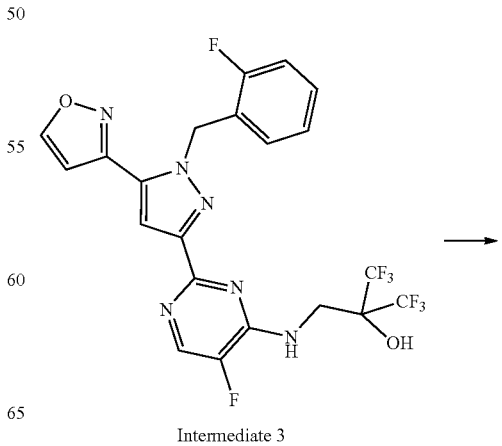

Intermediate 3

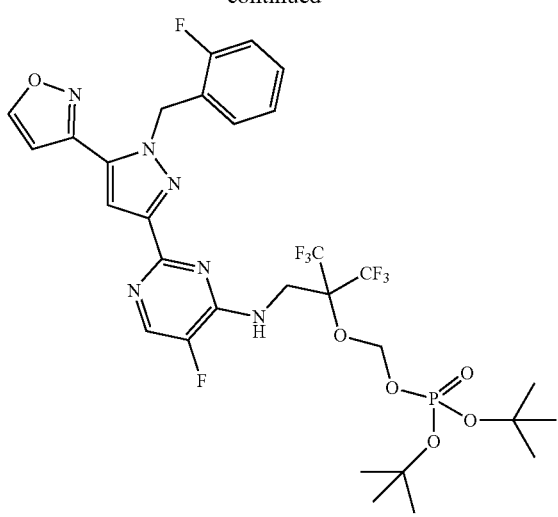

Intermediate 7

A mixture containing potassium carbonate (2.0 equiv.), tetrabutylammonium iodide (1.5 equiv.), Intermediate 3 (340 mg, 0.636 mmol) and di-tert-butyl (chloromethyl) phosphate (2.0 equiv.) in DMF (4.2 ml) was stirred at room temperature for 24 h. The mixture was diluted in ethyl acetate (50 ml). The organic layer was washed with water (50 ml×3), brine (50 ml), dried, filtered and evaporated to give an oil. The oil was purified by column chromatography utilizing a 0 to 100% ethyl acetate/hexanes gradient to give the title Intermediate 7 (201 mg, 42% yield) as a light yellow oil. This oil was used in the next step without further purification.

$^1$H NMR (500 MHz, CDCl$_3$) δ ppm 8.46 (d, 1H) 8.21 (d, 1H) 7.32 (s, 1H) 7.17-7.23 (m, 1H) 7.02 (ddd, 1H) 6.94-7.00 (m, 1H) 6.88-6.93 (m, 1H) 6.62 (d, 1H) 5.97 (s, 2H) 5.49 (d, 2H) 4.56 (d, 2H) 1.51 (s, 18H).

Step 2: Synthesis of Compound I-4

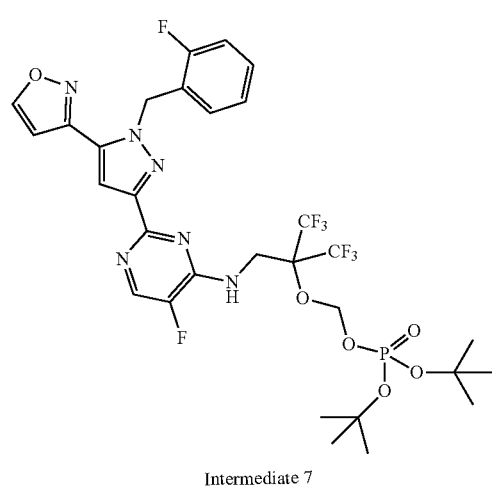

Intermediate 7

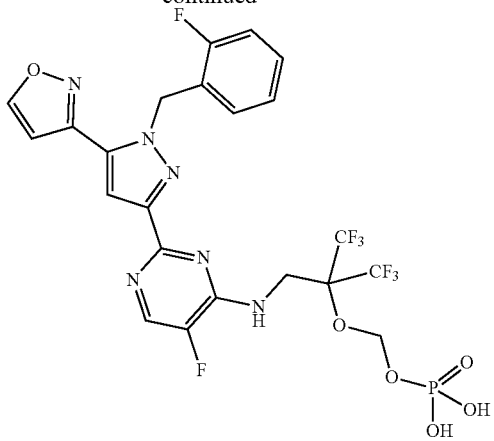

Compound I-4

A mixture containing Intermediate 7 (319 mg, 1.0 equiv.) and TFA (3.0 equiv.) in DCM (2.1 ml) was stirred at rt for 1 h. The mixture was concentrated in vacuo to give Compound I-4 (284 mg, quantitative yield) as a light yellow solid.

$^1$H NMR (500 MHz, CD$_3$OD) δ ppm 8.79-8.83 (m, 1H) 8.39 (d, 1H) 7.59 (s, 1H) 7.26-7.35 (m, 1H) 7.05-7.16 (m, 2H) 6.95-7.01 (m, 2H) 5.98-6.04 (m, 2H) 5.56 (d, 2H) 4.75 (s, 2H).

Disodium salt of Compound I-4

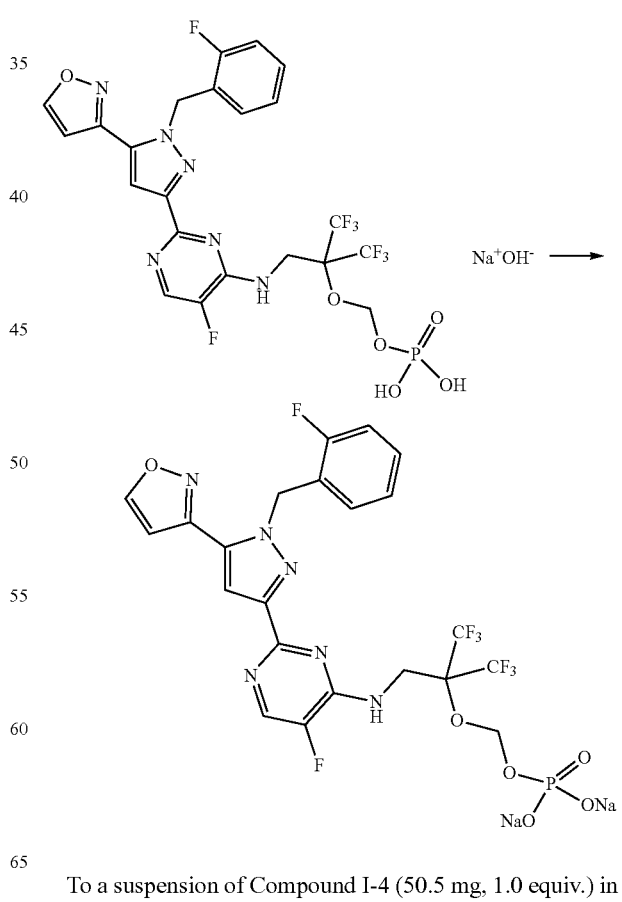

To a suspension of Compound I-4 (50.5 mg, 1.0 equiv.) in water (980 μl), was added a solution of sodium hydroxide as a 1.0 M aqueous solution (157 μl, 2.0 equiv.). Upon completion of the addition, the pH of the mixture was pH=7.4. The mixture was freeze-dried with a lyophilizer to give the title disodium salt of Compound I-4 (40.9 mg, 76% yield) as a white solid.

$^1$H NMR (500 MHz, D$_2$O) δ ppm 8.72 (s, 1H) 8.12 (d, 1H) 7.30-7.38 (m, 2H) 7.06-7.19 (m, 2H) 6.98 (t, 1H) 6.85 (s, 1H) 5.79 (s, 2H) 5.40 (d, 2H) 4.61 (s, 2H)

Compound I-5

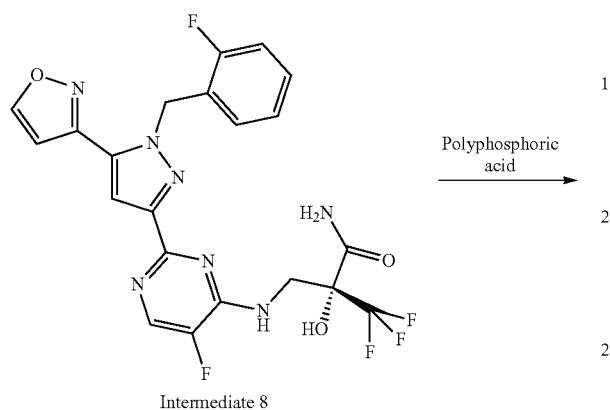

Intermediate 8

Polyphosphoric acid →

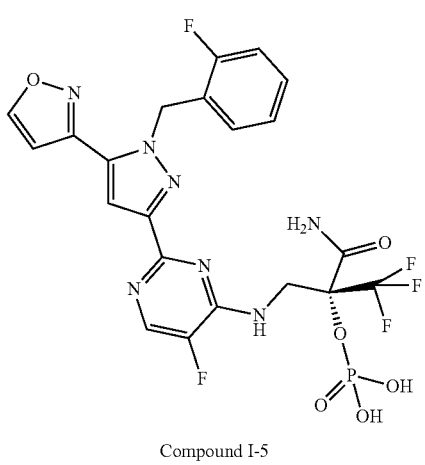

Compound I-5

A mixture containing Intermediate 8 (392 mg, 1.0 equiv., this compound was previously prepared as described in WO2014144100) and polyphosphoric acid (2.8 ml, 30 equiv.) was heated at 90° C. for 24 hours. The mixture was diluted in water and vigorously stirred for 3 hours until a slurry was formed. The pH of the mixture was raised to pH=4 by careful addition of sodium hydroxide (3.7 g, 120 equiv.). The light brown precipitate formed was collected by filtration. The precipitate obtained was purified by HPLC. The solid was dissolved in a mixture of 1,4-dioxane and water and freeze-dried in the lyophilizer to give the title Compound I-5 (4.7 mg, 1.0% yield) as a cream colored solid.

$^1$H NMR (D$_2$O) δ: 8.76 (br. s., 1H), 8.30 (br. s., 1H), 7.67 (s, 1H), 7.37 (br. s., 1H), 7.10-7.22 (m, 2H), 7.06 (d, 1H), 6.90 (br. s., 1H), 5.89 (br. s., 2H), 4.60-4.70 (m, 2H).

Compound I-2

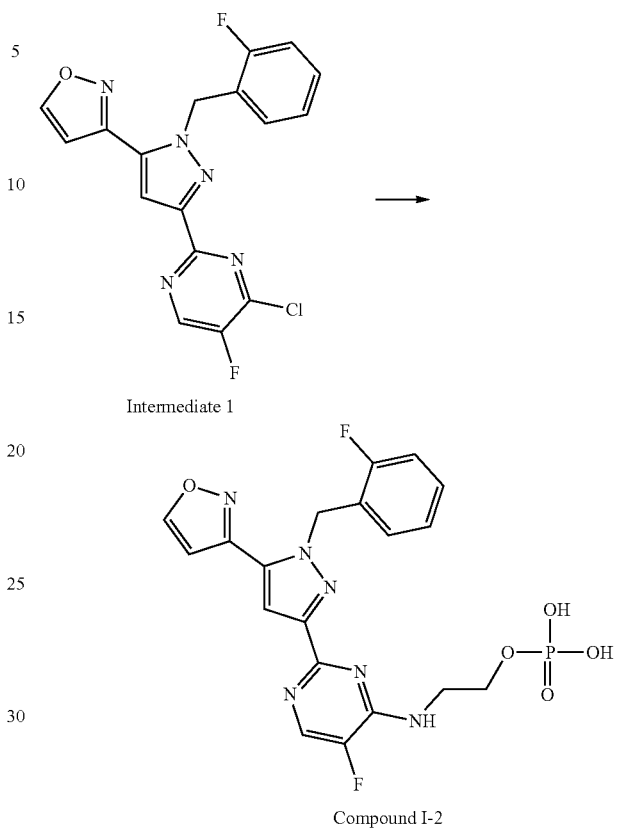

A solution of Intermediate 1 (26.9 mg, 0.191 mmol), ethanolamine phosphate (26.9 mg, 0.191 mmol) and triethylamine (0.0970 mL, 0.695 mmol) in dioxane (1 mL) and water (0.5 mL) was heated at 100° C. for 16 hours after which the reaction was cooled to room temperature and then diluted in 1N hydrochloric acid solution (0.400 mL), leading to the formation of a white precipitate which was predominantly unreacted starting material. This solid was filtered. Upon standing, another white solid started to precipitate out of the filtrate, which was also filtered, and was shown to be a mixture containing the desired product. This mixture was purified by reverse phase HPLC utilizing a gradient of 5 to 95% acetonitrile (spiked with 0.1 trifluoroacetic acid) in water over 25 minutes to afford the pure title Compound I-2 (21.3 mg, 26% yield), as a white solid.

$^1$H NMR (500 MHz, CD$_3$OD) δ (ppm): 8.81 (s, 1H), 8.22 (d, 1H), 7.66 (s, 1H), 7.28-7.32 (m, 1H), 7.09-7.12 (m, 1H), 7.04-7.07 (m, 1H), 6.99 (s, 1H), 6.92-6.95 (m, 1H), 6.02 (s, 2H), 4.21 (app. q, 2H), 3.99 (t, 2H). [ES]$^+$: calculated for C$_{19}$H$_{17}$F$_2$N$_6$O$_5$P, 478.10. Found: 0.97 min, 479.

Example 2A: Biological Activity Measurement by the sGC-HEK-cGMP Assay, with LC/MS Detection Human embryonic kidney cells (HEK293), endogenously expressing soluble guanylate cyclase (sGC), were used to evaluate the activity of test compounds. Compounds stimulating the sGC enzyme should cause an increase in the intracellular concentration of cGMP. HEK 293 cells were seeded in Dulbecco's Modification of Eagle's Medium supplemented with fetal bovine serum (10% final) and penicillin (100 U/mL)/streptomycin (100 μg/mL) in a 50 μL volume at a density of 1.5×10$^4$ cells/well in a poly-D-lysine coated 384 well flat bottom plate. Cells were incubated overnight at 37° C. in a humidified chamber with 5% $CO_2$. Medium was aspirated and cells were washed with 1×Hank's Buffered Saline Salt Solution (50 µL). Cells were then incubated for 15 minutes at 37° C. with 50 µL of a 0.5 mM 3-isobutyl-1-methylxanthine (IBMX) solution. The test article and Diethylenetriamine NONOate (DETA-NONOate) solutions (x µM concentration for test article solution and 10 µM concentration for DETA-NONOate solution; wherein x is one of the following concentrations)

| |
|---|
| 30000 nM |
| 7500 nM |
| 1875 nM |
| 468.75 nM |
| 117.19 nM |
| 29.29 nM |
| 7.32 nM |
| 1.83 nM |
| 0.46 nM |
| 0.114 nM |
| 0.029 nM | were then added to the assay mixture and the resulting mixture was incubated at 37° C. for 20 minutes. After the 20 minute incubation, the assay mixture was aspirated and 10% acetic acid containing 150 ng/mL+3-cGMP (internal standard for LCMS) (50 µL) was added to the cells. The plate was incubated at 4° C. for 30 minutes in the acetic acid solution to stop the reaction and lyse the cells. The plates were then centrifuged at 1,000 g for 3 minutes at 4° C. and the supernatant transferred to a clean reaction plate for LCMS analysis.

cGMP concentrations were determined from each sample using the LCMS conditions below (Table 2) and calculated standard curve. The standard curve was prepared in 10% acetic acid with 150 ng/mL+3cGMP (isotopically labelled cGMP with a weight 3 units higher than wild type) with the following final concentrations of cGMP in ng/mL: 1, 5, 10, 50, 100, 250, 500, 1000, 2000.

TABLE 2

| LC/MS conditions, Example 2A | | | | | |
|---|---|---|---|---|---|
| MS: | Thermo Vantage | | | | |
| Ion Mode: | ESI | | | | |
| Scan Type: | MRM | | | | |
| Compound: | Transition | Dwell Time (msec) | Collision Energy (V) | S Lens | Retention Time (min) |
| cGMP | 346 > 152 | 100 | 32 | 75 | 0.6 |
| (+3) cGMP IS | 349 > 155 | 100 | 32 | 75 | 0.6 |
| HPLC: | Waters Acquity UPLC | | | | |
| Column: | Thermo Hypersil Gold 2.1 × 50 mm 1.9 micron particle size | | | | |
| Flow Rate: | 750 uL/min | | | | |
| Column Temperature: | RT | | | | |
| Autosampler Temperature: | 6° C. | | | | |
| Injection Volume: | 20 uL | | | | |
| Mobile Phases: | A = 100% Water + 0.1% Formic Acid B = 100% Acetonitrile + 0.1% Formic Acid | | | | |
| | Time (min) | | % A | | % B |
| Gradient: | 0 | | 100 | | 0 |
| | 0.2 | | 100 | | 0 |
| | 0.3 | | 50 | | 50 |

TABLE 2-continued

| LC/MS conditions, Example 2A | | |
|---|---|---|
| 0.7 | 50 | 50 |
| 0.8 | 100 | 0 |

Data were normalized to a high control using the following equation: 100*(Sample−Low Control)/(High Control−Low Control), where the low control is the average of 16 samples treated with 1% DMSO, and the high control is the average of 16 samples treated with 30 µM of Compound Y depicted below. Data were fit using a 4-parameter fit (log (agonist) vs. response—variable slope) using GraphPad Prism Software v.5. n=2 for all compounds. The Absolute $EC_{50}$ was interpolated from the curve fit and is defined as the concentration at which a given compound elicits 50% of the high control response. Compounds failing to elicit a minimum response of 50% are reported as >30 µM. For compounds run in duplicate or n higher than 2, the result herein given is the geometric mean of the several results obtained.

Table 2A summarizes results obtained for selected compounds of the invention in this assay. As expected, prodrugs (for example Compound I-1 and Compound 14) did not exhibit a high degree of sGC agonism as compared to their parent drug.

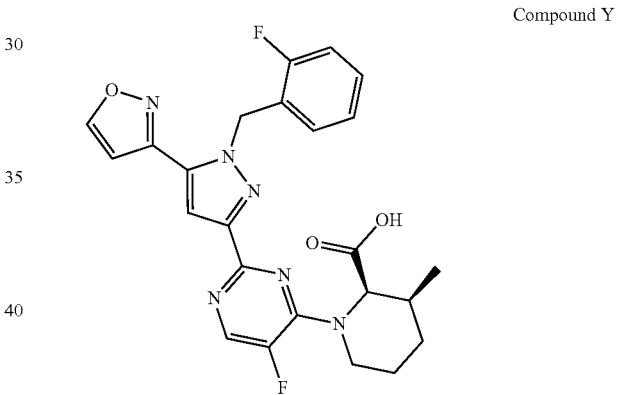

Compound Y

TABLE 2A

| Whole cell activity in the HEK assay with LC/MS detection | | | |
|---|---|---|---|
| Compound | Absolute EC50 (nM) | Parent compound | Absolute EC50 (nM) |
| I-1 | 12980 | Intermediate 3 | 220 |
| I-4 | 25000 | Intermediate 3 | 220 | sGC enzyme activity values in HEK cells, expressed as Absolute $EC_{50}$ which is defined as the concentration at which a given compound elicits 50% of the high control response obtained with Compound Y, after normalization.

Example 2B: Biological Activity Measurement by the cGMP GloSensor Cell-Based Assay, 384-Well Format Human embryonic kidney cells (HEK293) cells expressing GloSensor™ 40F cGMP (Part No: CS182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GloSensor cells were maintained in Dulbecco's Modification of Eagle's Medium (DMEM) supplemented with fetal bovine serum (FBS, 10% final) and hygromycine (200 ug/ml). The day before assay, cells were plated in DMEM with 10% FBS in a 50 µL volume at a density of $1.5 \times 10^4$ cells/well in a poly-D-lysine coated 384-well flat white-bottom plate (Corning Cat. No. 35661). Cells were incubated overnight at 37° C. in a humidified chamber with 5% $CO_2$. The next day, medium was removed and cells were replaced with 40 ul/well of GloSensor™, 2 mM (Promega Cat No E1291). Cells were treated for 90 minutes at 25° C. to allow the substrate to equilibrate in the cells. Test compounds and Diethylenetriamine NONOate (DETA-NONOate) was diluted to 3 mM (20×) in serum-free $CO_2$ independent medium and serially diluted at 4× dilutions to create 5× dose curve from which 10 ul was added to the wells (x µM concentration for test compound solution and 10 µM concentration for DETA-NONOate solution; wherein x is one of the following final concentrations).

| |
|---|
| 30000 nM |
| 7500 nM |
| 1875 nM |
| 468.75 nM |
| 117.19 nM |
| 29.29 nM |
| 7.32 nM |
| 1.83 nM |
| 0.46 nM |
| 0.114 nM |
| 0.029 nM |

For the kinetics studies, luminescence was measured right away for 0.2 sec per well with Envision (Perkin Elmer). For endpoint SAR screening, data were collected after 55 min incubation at room temperature.

Data analysis was carried out as indicated above in Example 2A.

As expected, prodrugs (for example Compound I-1) did not exhibit a high degree of sGC agonism as compared to their parent drug.

TABLE 2B

Whole cell activity in the GloSensor cell-based assay, 384-well format (Example 2B)

| Compound | Absolute EC50 (nM) | Parent compound | Absolute EC50 (nM) |
|---|---|---|---|
| I-1 | 4843 | Intermediate 3 | 72 | sGC enzyme activity values in HEK cells, determined by the GloSensor assay, expressed as Absolute $EC_{50}$ which is defined as the concentration at which a given compound elicits 50% of the high control response obtained with Compound Y, after normalization.

Example 3: Thermodynamic Solubility Measurements

Approximately 1 mg of test compound was weighed into 1.5 mL Eppendorf tubes and 1.5 mL of aqueous buffer of a given pH was added. The samples were vortexed and placed on a shaker at 150 RPM for 2-5 days. The samples were harvested and then centrifuged at 12 K RPM for 20 minutes. The supernatant was diluted twice with Acetonitrile (ACN) and analyzed by UPLC. To dilute the samples, 200 uL of supernatant was taken and discarded. Then, 400 uL of supernatant (with 200 uL intervals) was taken and added to 400 uL of acetonitrile (with 200 uL intervals).

UPLC conditions: Mobile Phase A: 0.1% TFA in Water; Mobile Phase B: 0.1% TFA in Acetonitrile; Column: Acquity BEH C18, 1.7 um, 2.1×50 mm; Injection Volume: 2-3 uL; Autosampler Temperature: Ambient; Column Temperature: 25° C.; Run Time: 10 minutes; Flow Rate: 0.45 mlJmin; Collected Wavelengths: 220 nm, 245 nm, 254 nm, 280 nm, PDA Spectrum (190-400 nm); Wavelength Used for Analysis: 254 nm
Gradient (Table 3):

| Time (min) | % MPA | % MPB |
|---|---|---|
| 0.00 | 90.0 | 10.0 |
| 1.00 | 90.0 | 10.0 |
| 7.50 | 20.0 | 80.0 |
| 8.50 | 20.0 | 80.0 |
| 8.60 | 90.0 | 10.0 |
| 10.00 | 90.0 | 10.0 |

Solubility of Compound I-1=66-1000 µg/mL at pH 7
Solubility of Compound I-4=71 g/mL at pH 7
Solubility of Parent Intermediate 3=2-3 g/mL at pH 7

Example 4: Ex-Vivo Rat Intestinal Fluid Stability Assay

Phosphate prodrugs disclosed herein were designed to be cleaved by alkaline phosphatase(s) that are present on the apical brush-border membranes of the intestine, after which the more hydrophobic parent compound is readily absorbed. Phosphatases are also present in the liver and in the systemic circulation. In order to test the speed of cleavage of the prodrug into the parent drug, 5 M solutions of each of the test compounds were incubated in rat intestinal (jejunum) fluid. Samples were taken at times=0, 5, 15, 30 and 60 min and the mixtures were quenched by the addition of acetonitrile containing an internal standard. Samples were analyzed by full scan LC/MS. The following protocol was used:
Preparation of Solutions and Materials 10 mM DMSO stock solutions were thawed or prepared for the positive control (Enalapril) and each test article. Internal standard (IS) crash solution in acetonitrile (ACN) with 20 ng/ml of Compound Z, depicted below, was prepared. Stock (250 uM) was prepared from 10 mM in 50/50 acetonitrile/$H_2O$. Rat intestinal fluid vials were thawed in a water bath at rt.

Compound Z

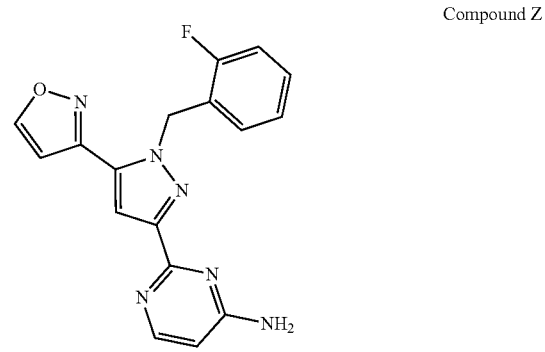 [SMILES: Nc1ccnc(-c2cc(-c3ccon3)n(Cc3ccccc3F)n2)n1]

Intestinal Fluid Sample Preparation

In a 96-well, 1 ml plate, 48 uL of rat intestinal fluid was aliquoted in triplicate for each time point. The $t_0$ ("0 min") time point was prepared separately by adding 450 ul of IS crash solution to 48 ul of intestinal fluid, then adding 2 uL of test compound. 2 ul of the 250 uM substock was added to initiate the reaction at 5 min, 15 min, 30 min, and 60 min. The plate prepared in the above steps was covered with a plastic or foil seal and was set in the 37° C. incubator, lightly shaking. For each time point, 450 ul of IS crash solution was added to quench the reaction. The plates were centrifuged at 4000 RPM for 10 minutes at 4° C. 50 ul of supernatant was transferred into 50 ul of $H_2O$ and analyzed using LC/MS.

The disappearance of the prodrug and the conversion to the parent were monitored over time. The following LC/MS protocol was used (Table 4):

| LC Method (based on the Waters Acquity system) | |
|---|---|
| Column: | Thermo Hypersil Gold C18, 2.1 × 30 mm, 5 um |
| Guard Column: | Thermo Hypersil Gold C18 Javelin |
| Column Temp: | 25° C. |
| Flow Rate: | 0.4 mL/min |
| Autosampler: | Acquity; 6° C. |
| Injection Volume: | 10 uL |
| Mobile Phases: | A = 0.1% formic acid (v/v) in 95:5 water:ACN |
| | B = 0.1% formic acid (v/v) in 5:95 water:ACN |

| | Time (min) | % A | % B |
|---|---|---|---|
| Gradient: | 0 | 95 | 5 |
| | 0.5 | 95 | 5 |
| | 1.0 | 40 | 60 |
| | 2.5 | 5 | 95 |
| | 2.5 | 5 | 95 |
| | 3.0 | 95 | 5 |
| | 3.5 | (end) | |

| MS Method (based on the Waters Synapt TOF) | | | |
|---|---|---|---|
| Ionization: | ES⁺ | | |
| Source, Desolvation: | 125° C., 500° C. | Capillary | 3.0 kV |
| MS Function: | Full scan MS | | |
| Mode: | Sensitivity | | |

For comparison purposes, several marketed phosphate prodrugs were used as benchmarks in this assay: fosphenytoin and fostamatinib (known to cleave to the parent drug quickly in vivo) and fosfluconazole (a phosphate ester prodrug of a tertiary alcohol, known to cleave slowly to the parent drug in vivo).

Under the experimental conditions, fosphenytoin was rapidly cleaved to its parent drug. More than 80% of the prodrug had been converted into its parent drug after 30 minutes of incubation. After 60 minutes of incubation, no prodrug could be detected. In this rat intestinal fluid assay, the disappearance half-life ($T_{1/2}$) was determined to be 5 min. The human half-life (from published data) has been reported to be 8-15 min (Fosphenytoin: a novel phenytoin prodrug. Boucher BA, Pharmacology, 1996 September-October; 16(5): 777-91).

Under the experimental conditions, fostamatinib was moderately rapidly cleaved to its parent drug. About 50% of the prodrug had been converted into its parent drug after 30 minutes of incubation. About 80% of the prodrug had been converted into its parent drug after 60 minutes of incubation. In this rat intestinal fluid assay, the disappearance half-life ($T_{1/2}$) was determined to be 34 min. When human microsomes were used, the prodrug has been reported to be fully hydrolized after 15 min ("Metabolism of Fosfamatinib, the Oral Methylene Phosphat Prodrug of the Spleen Tyrosine Kinase Inhibitor $R^{406}$ in Humans: Contribution of Hepatic and Gut Bacterial Processes to the Overal Transformacion". DJ Sweeny et al. Drug Metabolism and Disposition, 38, 1166-1176 (2010)). In human clinical trials, no quantifiable fostamatinib was observed in any subject after the 2-hour time point ("Pharmacokinetics of fostamatinib, a spleen tyrosine kinase (SYK) inhibitor, in healthy human subjects following single and multiple oral dosing in three phase I studies". Muhammad Baluom, Elliott B Grossbard, Tim Mant and David T W Lau Br J Clin Pharmacol. 2013 July; 76(1): 78-88)

Under the experimental conditions, and as expected due to being a sterically hindered tertiary alcohol, fosfluconazole was more slowly cleaved to its parent drug. About 80% of the prodrug remained uncleaved after 60 minutes of incubation. In this rat intestinal fluid assay, the disappearance half-life (T1/2) was determined to be 211 min. The human half-life (from published data) has been reported to be 1.5-2.5 hours ("Pharmacokinetics of fosfluconazole and fluconazole following multiple intravenous administration of fosfluconazole in healthy male volunteers". Sobue S, Tan K, Layton G, Eve M, and Sanderson $J^B$. Br J Clin Pharmacol 58:20-25, (2004).

See "Evaluation of in Vitro Models for Screening Alkaline Phosphatase-Mediated Bioconversion of Phosphate Ester Prodrugs" Haodan Yuan, Na Li, and Yurong Lai; Drug Metabolism and Disposition 37:1443-1447, 2009 for comparison of the cleavage times of phophenytoin vs. fosfluconazole in several in-vitro models.

Unexpectedly, Compound I-1, the phosphate ester prodrug of tertiary alcohol Intermediate 3, was cleaved quite rapidly. About 80% of the prodrug had been converted to its parent drug after 30 minutes of incubation and about 95% of the prodrug had been cleaved after 60 minutes of incubation. In this rat intestinal fluid assay the disappearance half-life ($T_2$) was determined to be 16 min.

Compound I-4, another phosphate ester prodrug of tertiary alcohol Intermediate 3, also was cleaved quite unexpectedly rapidly. More than 99% of the prodrug had been cleaved after 60 minutes of incubation. In this rat intestinal fluid assay the disappearance half-life ($T_2$) was determined to be 9 min.

Also unexpectedly, phosphate prodrug Compound I-3 of Intermediate 2 (a tertiary alcohol) was cleaved rapidly. After 30 minutes of incubation, about 25% of the prodrug had been consumed. After 60 minutes of incubation, less than 10% of the prodrug remained in solution.

Example 5: Rat PK Compound I-1 (Compared to its Parent Intermediate 3)

Protocol

PK in rats was determined following intravenous and oral dosing.

For the intravenous (IV) and oral (PO) experiments, two groups of 4 male Sprague-Dawley rats each were used. The PO group was dosed with 3.0 mg/kg of Compound I-1 formulated as a solution in phosphate buffered saline (PBS). The IV group was dosed with 1.0 mg/kg of Compound I-1 formulated as a solution in phosphate buffered saline (PBS). IV doses were administered through an indwelling catheter in the jugular vein. Following dose administration, the catheter was flushed with ca. 0.25 mL of saline. PO doses were delivered to the stomach using a syringe and gavage tube. Following oral dosage administration, the gavage tube was flushed with approximately 0.5 mL of water to ensure complete delivery of the full dose.

Plasma samples were collected as follows: for the IV and PO experiments, samples were collected at 5 min, 15 min, 30 min, 1 hour, 2 hours, 4 hours, 6 hours, 8 hours, 12 hours, 16 hours, 20 hours and 24 hours, post-dosing. Blood samples (0.25 mL) were collected from the jugular vein. These samples were kept on ice until processed for plasma. Blood samples were centrifuged at 3200 rpm for 5 minutes at approximately 5° C. within 1 hour of collection. Plasma was directly transferred to a 96-well plate tube (0.125 mL). Plug caps were placed on the tubes and the tubes frozen at approximately −70° C. and stored until analysis.

Plasma was collected and analyzed for the presence of Compound I-1 and Intermediate 3 derived from Compound I-1.

Quantitation of Compound I-1 and Intermediate 3 by LC-MS/MS

Intermediate 3, Compound I-1 and the internal standard (IS, Compound Z) were extracted from plasma by precipitation. Samples were analyzed using liquid chromatography (LC) with tandem mass spectrometric detection (MS/MS) using electrospray ionization. The standard curve range was from 0.1 to 400 ng/mL.

Preparation of Stock Solutions (Stored Solutions at 4° C.)

Intermediate 3 DMSO Stock Solution (1 mg/mL): dissolved with DMSO to a final concentration of 1 mg/mL.

Compound I-1 DMSO Stock Solution (1 mg/mL): dissolved with DMSO to a final concentration of 1 mg/mL.

Preparation of Working Solutions (Prepared Fresh)

Intermediate 3 (50 ug/mL) working solution: prepared 1 mL of a 50 ug/mL working solution from the 1 mg/mL stock standard solution by adding 50 ul to 950 ul of ACN.

Compound I-1 (50 ug/mL) working solution: prepared 1 mL of a 50 ug/mL working solution from the 1 mg/mL stock standard solution by adding 50 ul to 950 ul of ACN.

Preparation of Standards

Created 100× standard curves of Intermediate 3 (in ACN) and Compound I-1(in ACN). Stored the solutions at −80° C.

Preparation of Standards, Samples and Blanks

Thawed plasma samples and the required amount of plasma for standards, blanks and dilutions. Prepared crash solution: room temp ACN containing 1 ng/mL Compound Z as Internal Standard. Created a 1× mixed (Intermediate 3 and Compound I-1) standard curve by diluting the 100× stocks (5 uL of each 100× standard into 495 uL of plasma). Transferred 50 uL of each plasma sample/dilution, standard, or blank. Added 200 uL of the crash solution containing IS. Vortexed for 5 minutes. Centrifuged at 16,000 g at room temperature for 10 min. Transferred 200 uL of each supernatant to a plate. Dried under nitrogen in a TurboVap at 55° C. Re-suspended each sample in 50 uL of 0.1% Formic Acid, covered and vortexed. Analyzed by LC-MSMS. The following conditions were used (Table A):

TABLE 5A

| MS: | SCIEX/Applied Biosystems API 5500 QTRAP | | | | |
|---|---|---|---|---|---|
| Ion Mode: | ESI$^+$ | | | | |
| Scan Type: | MRM | | | | |
| Compound: | Transition | Dwell Time (msec) | Declustering Potential (V) | Collision Energy (V) | Cell Exit Potential (V) | Retention Time (min) |
| Compound I-1 | 615 > 535 | 50 | 90 | 28 | 17 | 1.7 |
| Intermediate 3 | 535 > 109.0 | 50 | 160 | 23 | 12 | 1.8 |
| Compound Z (IS) | 337.0 > 109.0 | 50 | 70 | 30 | 15 | 1.6 |

| | Curtain Gas: | IS: | GS1: | GS2: | Temp. | CAD: | EP: |
|---|---|---|---|---|---|---|---|
| MS Parameters: | 20 | 1500 | 50 | 50 | 650° C. | 5 | 10 |

| Resolution: | Q1: unit | Q3: unit |
|---|---|---|
| HPLC: | Water's Acquity UPLC | |
| Column: | Phenomenex Kinetex XB C18, 3.0 × 100 mm, 5 um (PN: 00D-4605-Y0) | |
| Flow Rate: | 0.5 mL/min | |
| Column Temperature: | 25° C. | |
| Autosampler: | 6° C. | |
| Injection Volume: | 2 uL | |
| Mobile Phases: | A = 0.1% FA in water B = acetonitrile | |

| | Time (min) | % A | % B |
|---|---|---|---|
| Gradient: | 0 | 100 | 0 |
| | 0.5 | 100 | 0 |
| | 2.00 | 0 | 100 |
| | 2.01 | 100 | 0 |
| | 4 | 100 | 0 |

Results

The results of the IV Rat PK experiment are summarized in the Table 5B below

| Compound (1 mg/kg IV) | Compound I-1 (in PBS) | Intermediate 3 from Compound I-1 (in PBS) | Intermediate 3 (in PEG) |
|---|---|---|---|
| Half-life | 8.8 min | 5.2 h | 7.1 h |
| Cmax (ng/mL) | 2777.2 ± 2445.5 | 88.6 | 227 |
| Vol. of Dist (L/kg) | 4.4 ± 2.6 | 13.1 | 9.5 |

-continued

| Compound (1 mg/kg IV) | Compound I-1 (in PBS) | Intermediate 3 from Compound I-1 (in PBS) | Intermediate 3 (in PEG) |
|---|---|---|---|
| Clearance (mL/min/kg) | 34.3 | 20.4 | 16 |
| AUC$_{0\text{-}inf}$ (h * ng/mL) | 548.7 | 759.22 | 1100 |

The Compound I-1 prodrug cleanly converted to its parent Intermediate 3 with a half-life of about 9 minutes when administered IV. Compound I-1 dosed IV in PBS (phosphate buffered saline) gave comparable PK parameters to Intermediate 3(its parent) dosed in PEG.

The results of the Oral (PO) Rat PK experiment are summarized in the Table 5C below:

| | Compound | Compound I-1 | Intermediate 3 generated from Compound I-1 | Intermediate 3 |
|---|---|---|---|---|
| 3.0 mg/kg PO | $C_{max}$ (ng/mL) | — | 94 ± 39 | 250 ± 10 |
| | $T_{max}$ (h) | — | 7.3 ± 1.2 | 8 |
| | AUC$_{0\text{-}last}$ (min * ng/mL) | — | 920 ± 230 | 3600 ± 280 |
| | Bioavail. (%) | — | 60 | 102 |
| | HEK EC$_{50}$ (µM) | — | 0.1 | 0.1 |

Prodrug Compound I-1 was not observed in any plasma samples following PO dosing. $T_{max}$ for Intermediate 3 generated from Compound I-1 was observed to be about 7 hours, similar to the $T_{max}$ for the parent drug Intermediate 3 following a similar administration.

Example 6: Dog PK Compound I-1 (Compared to its Parent Intermediate 3)

Protocol

PK in dogs was determined following IV and oral dosing.

For the oral (PO) experiments, two groups of 5 male Beagle dogs each were used. One group was dosed with 2.5 mg/kg of Compound I-1 formulated as PEG400 solution in capsules. The other group was dosed with 2.5 mg/kg of Compound I-1 formulated as a PBS solution. For the IV experiments, 5 male Beagle dogs were dosed with 0.5 mg/kg of Compound I-1 formulated as a PBS solution. IV doses were administered through an indwelling catheter in the cephalic vein. Following dose administration, the catheter was flushed with ca. 3 mL of saline. Oral suspension doses were delivered to the stomach using a syringe and gavage tube. Following oral dosage administration, the gavage tube was flushed with approximately 10 mL of water to ensure complete delivery of the full dose.

Plasma and urine samples were collected as follows: for the PO experiments, samples were collected at 15 min, 30 min, 1 hour, 2 hours, 3 hours, 4 hours, 6 hours, 8 hours, 24 hours, 32 hours and 48 hours post-dosing; for the IV experiments, samples were collected at 2 min, 5 min, 15 min, 30 min, 1 hour, 2 hours, 3 hours, 4 hours, 6 hours, 8 hours, 24 hours, 32 hours and 48 hours post-dosing. Blood samples (2 mL) were collected from the jugular, cephalic or saphenous veins. These samples were kept on ice until processed for plasma. Blood samples were centrifuged at 3200 rpm for 10 minutes at approximately 5° C. within 1 hour of collection. Plasma was split into two approximately equal aliquots, and directly transferred to a 96-well plate tube (1.1 mL). Plug caps were placed on the tubes and the tubes frozen at approximately −70° C. and stored until analysis.

Urine was collected from each animal by diversion from a urine collection pan placed beneath the cage of each animal into an appropriate collection container, surrounded by wet ice or ice packs throughout the collection. The total volume of urine collected at each interval was measured and recorded and a single 10 mL aliquot was collected and stored frozen at approximately −70° C. until analysis.

Plasma and urine were collected and analyzed for the presence of Compound I-1 and Intermediate 3 derived from Compound I-1.

Quantitation of Compound I-1 and Intermediate 3 by LC-MS/MS

Intermediate 3, Compound I-1 and the internal standard (IS, Compound Z) were extracted from plasma by precipitation. Samples were analyzed using liquid chromatography (LC) with tandem mass spectrometric detection (MS/MS) using electrospray ionization. The standard curve range was from 0.1 to 400 ng/mL.

Preparation of Stock Solutions (Stored Solutions at 4° C.)

Intermediate 3 DMSO Stock Solution (1 mg/mL): dissolved with DMSO to a final concentration of 1 mg/mL.

Compound I-1 DMSO Stock Solution (1 mg/mL): dissolved with DMSO to a final concentration of 1 mg/mL.

Preparation of Working Solutions (Prepared Fresh)

Intermediate 3 (50 ug/mL) working solution: prepared 1 mL of a 50 ug/mL working solution from the 1 mg/mL stock standard solution by adding 50 ul to 950 ul of ACN.

Compound I-1 (50 ug/mL) working solution: prepared 1 mL of a 50 ug/mL working solution from the 1 mg/mL stock standard solution by adding 50 ul to 950 ul of ACN.

Preparation of Standards

Created 100× standard curves of Intermediate 3 (in ACN) and Compound I-1(in ACN). Stored them at −80° C.

Preparation of Standards, Samples and Blanks

Thawed plasma samples and the required amount of plasma for standards, blanks and dilutions. Prepared crash solution: room temp ACN containing 1 ng/mL Compound Z as Internal Standard. Created a 1× mixed (Intermediate 3 and Compound I-1) standard curve by diluting the 100× stocks (5 uL of each 100× standard into 490 uL of plasma). Transferred 50 uL of each plasma sample/dilution, standard, or blank. Added 200 uL of the crash solution containing IS. Vortexed for 5 minutes. Centrifuged at 16,000 g at room temperature for 10 min. Transferred 200 uL of each supernatant to a plate. Dried under nitrogen in a TurboVap at 55° C. Resuspended each sample in 50 uL of 0.1% Formic Acid, covered and vortexed. Analyzed by LC-MS/MS. The following conditions were used:

TABLE 6A

| | | Dwell Time (msec) | Declustering Potential (V) | Collision Energy (V) | Cell Exit Potential (V) | Retention Time (min) |
|---|---|---|---|---|---|---|
| MS: | SCIEX/Applied Biosystems API 5500 QTRAP | | | | | |
| Ion Mode: | ESI+ | | | | | |
| Scan Type: | MRM | | | | | |
| Compound: | Transition | | | | | |
| Compound I-1 | 615 > 535 | 50 | 90 | 28 | 17 | 1.7 |
| Intermediate 3 | 535 > 109.0 | 50 | 160 | 23 | 12 | 1.8 |
| Compound Z (IS) | 337.0 > 109.0 | 50 | 70 | 30 | 15 | 1.6 |

| | Curtain Gas: | IS: | GS1: | GS2: | Temp. | CAD: | EP: |
|---|---|---|---|---|---|---|---|
| MS Parameters: | 20 | 1500 | 50 | 50 | 650° C. | 5 | 10 |

| | | |
|---|---|---|
| Resolution: | Q1: unit | Q3: unit |
| HPLC: | Water's Acquity UPLC | |
| Column: | Phenomenex Kinetex XB C18, 3.0 × 100 mm, 5 um (PN: 00D-4605-Y0) | |
| Flow Rate: | 0.5 mL/min | |
| Column Temperature: | 25° C. | |
| Autosampler: | 6° C. | |
| Injection Volume: | 2 uL | |
| Mobile Phases: | A = 0.1% FA in water | |
| | B = acetonitrile | |

| | Time (min) | % A | % B |
|---|---|---|---|
| Gradient: | 0 | 100 | 0 |
| | 0.5 | 100 | 0 |
| | 2.00 | 0 | 100 |
| | 2.01 | 100 | 0 |
| | 4 | 100 | 0 |

Results

The results of the IV Dog PK experiment are summarized in the Table 6B below:

| Compound | Compound I-1 (0.36 mpk IV in PBS) | Intermediate 3 from Compound I-1 (PBS) |
|---|---|---|
| Half-life | 15 min | Tmax: 30 min |
| Cmax (ng/mL) | 5110 ± 2146 | 129 ± 23 |
| Vol. of Dist. (L/kg) | 0.09 ± 0.03 | 13.1 |
| Clearance (mL/min/kg) | 8.3 ± 3.1 | |
| $AUC_{0\text{-}inf}$ (h * ng/mL) | 1548 ± 601 | 1576 ± 472 |

The Compound I-1 prodrug cleanly converted to its parent Intermediate 3 with a half-life of about 15 minutes when administered IV. Conversion to the parent was rapid with an average conversion of 95%. Compound I-1 dosed IV in PBS gave comparable AUC to Intermediate 3 (its parent) dosed in PEG.

The results of the Oral (PO) Dog PK experiment are summarized in the Table 6C below:

| | Intermediate 3 from Compound I-1 in PBS (2.2 mg/kg) | Intermediate 3 in PEG400 capsules (2 mg/kg) |
|---|---|---|
| Cmax (ng/mL) | 365 ± 18 | 307 ± 116 |
| Tmax (hr) | 1.8 ± 0.4 | 1.5 ± 1.2 |
| Bioavailability (% F) | 51 ± 14 | 64 ± 12.5 |
| Cmax/C24 (ratio) | 5.8 ± 1.7 | 3.6 ± 1.1 |
| AUC All (h * ng/mL) | 4392 ± 972 | 5190 ± 1406 |

The bioavailability of Intermediate 3 from Compound I-1 in PEG400-filled capsules was similar to that of the parent Intermediate 3 in the same formulation. Low levels of the prodrug were observed in plasma after PO administration. Negligible amounts of the prodrug were also found in urine of the animals used in this experiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A compound of Formula I:

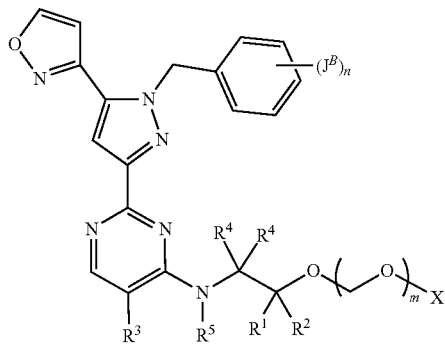

Formula I or a pharmaceutically acceptable salt thereof, wherein:
each $J^B$ is independently halogen;
$R^1$ is hydrogen, $C_{1-4}$ alkyl, $C_{1-4}$ fluoroalkyl, or $-C(O)NH_2$;
$R^2$ is hydrogen, $C_{1-4}$ alkyl, or $C_{1-4}$ fluoroalkyl; or
$R^1$ and $R^2$, together with the carbon atom to which they are attached, form an unsubstituted $C_{3-7}$ cycloaliphatic ring or an unsubstituted 3- to 7-membered heterocyclic ring, wherein the heterocyclic ring contains 1 or 2 heteroatoms independently selected from the group consisting of nitrogen, oxygen, and sulfur;
$R^3$ is hydrogen, halogen, cyano, or $-NH_2$;
each $R^4$ is independently hydrogen; or
two $R^4$, together with the carbon atom to which they are attached, form a carbonyl;
$R^5$ is hydrogen or methyl;

X is:

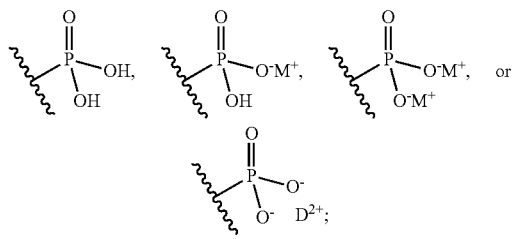

$M^+$ is a pharmaceutically acceptable monovalent cation;
$D^{2+}$ is a pharmaceutically acceptable divalent cation;
m is 0 or 1; and
n is 0, 1, 2, 3, or 4.

2. The compound according to claim 1, or a pharmaceutically acceptable salt thereof, wherein:
(i) $R^1$ is $C_{1-4}$ fluoroalkyl; and
$R^2$ is $C_{1-4}$ fluoroalkyl; or
(ii) R is $C_{1-2}$ fluoroalkyl; and
$R^2$ is $C_{1-2}$ fluoroalkyl; or
(iii) $R^1$ is trifluoromethyl; and
$R^2$ is trifluoromethyl.

3. The compound according to claim 1, or a pharmaceutically acceptable salt thereof, wherein $R^3$ is hydrogen, fluoro, or chloro.

4. The compound according to claim 3, or a pharmaceutically acceptable salt thereof, wherein $R^3$ is fluoro.

5. The compound according to claim 1, or a pharmaceutically acceptable salt thereof, wherein X is:

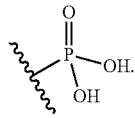

6. The compound according to claim 1, or a pharmaceutically acceptable salt thereof, wherein:
X is:

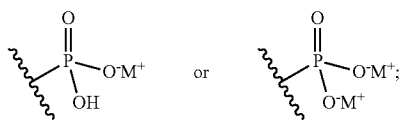

and
$M^+$ is $Na^+$, $K^+$, $Cs^+$, or the monovalent cation of an organic amine.

7. The compound according to claim 1, or a pharmaceutically acceptable salt thereof, wherein:
X is:

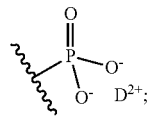

and
$D^{2+}$ is $Mg^{2+}$, $Ca^{2+}$, $Zn^{2+}$, or the divalent cation of an organic amine.

8. The compound according to claim 1, or a pharmaceutically acceptable salt thereof, wherein m is 0.

9. The compound according to claim 1, or a pharmaceutically acceptable salt thereof, wherein m is 1.

10. The compound according to claim 1, or a pharmaceutically acceptable salt thereof, wherein n is 0, 1, or 2.

11. The compound according to claim 10, or a pharmaceutically acceptable salt thereof, wherein:
(i) each $J^B$ is independently fluoro; or
(ii) each $J^B$ is independently chloro; or
(iii) each $J^B$ is independently chloro or fluoro.

12. The compound according to claim 1, wherein the compound is of Formula V:

Formula V or a pharmaceutically acceptable salt thereof.

13. The compound according to claim 1, wherein the compound is of Formula VI:

Formula VI or a pharmaceutically acceptable salt thereof.

14. The compound according to claim 1, wherein the compound is:

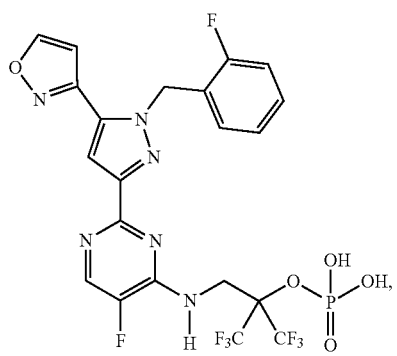 [SMILES: O=P(O)(O)OC(CNc1nc(-c2cc(-c3ccon3)n(Cc3ccccc3F)n2)ncc1F)(C(F)(F)F)C(F)(F)F]

or a pharmaceutically acceptable salt thereof.

15. The compound according to claim 1, wherein the compound is:

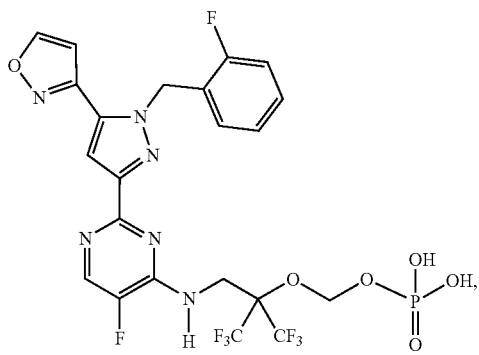 [SMILES: O=P(O)(O)OCOC(CNc1nc(-c2cc(-c3ccon3)n(Cc3ccccc3F)n2)ncc1F)(C(F)(F)F)C(F)(F)F]

or a pharmaceutically acceptable salt thereof.

16. A pharmaceutical composition comprising one or more excipients and a compound according to claim 1, or a pharmaceutically acceptable salt thereof.

* * * * *